US00RE50293E

(19) United States
(12) Reissued Patent
Noda

(10) Patent Number: US RE50,293 E
(45) Date of Reissued Patent: Feb. 4, 2025

(54) TINNITUS TREATMENT DEVICE AND RECORDING MEDIUM

(71) Applicant: Kazuhiro Noda, Osaka (JP)

(72) Inventor: Kazuhiro Noda, Osaka (JP)

(21) Appl. No.: 17/974,065

(22) Filed: Oct. 26, 2022

Related U.S. Patent Documents

Reissue of:
(64) Patent No.: 11,228,854
Issued: Jan. 18, 2022
Appl. No.: 17/292,256
PCT Filed: Nov. 15, 2018
PCT No.: PCT/JP2018/042361
§ 371 (c)(1),
(2) Date: May 7, 2021
PCT Pub. No.: WO2020/100270
PCT Pub. Date: May 22, 2020

(51) Int. Cl.
*H04R 25/00* (2006.01)

(52) U.S. Cl.
CPC ..... *H04R 25/75* (2013.01); *H04R 25/50* (2013.01)

(58) Field of Classification Search
CPC .... H04R 25/75; H04R 25/50; H04R 2225/83; H04R 25/70; H04R 29/00; H04R 2225/81
See application file for complete search history.

(56) References Cited

U.S. PATENT DOCUMENTS 2,605,361 A 7/1952 Cutler
2009/0099476 A1 4/2009 Fogel et al.
2011/0105967 A1 5/2011 Zeng et al.
2012/0283593 A1* 11/2012 Searchfield ..... H04R 25/75 600/559
2015/0003635 A1 1/2015 Baker et al.

FOREIGN PATENT DOCUMENTS

| | | |
|---|---|---|
| CN | 203915229 | 11/2014 |
| JP | 2011-505915 | 3/2011 |
| WO | 02/096154 | 11/2002 |
| WO | 2009/076191 | 6/2009 |

OTHER PUBLICATIONS

International Search Report (ISR) issued on Jan. 22, 2019 in International (PCT) Application No. PCT/JP2018/042361.
Inui, K., Urakawa, T., Yamashiro, K., Otsuru, N., and Nishihara, M., (2010), "Non-linear laws of echoic memory and auditory change detection in humans", BMC Neuroscience, 11: 80.
(Continued)

*Primary Examiner* — Robert L Nasser
(74) *Attorney, Agent, or Firm* — Wenderoth, Lind & Ponack, L.L.P.

(57) ABSTRACT

A tinnitus treatment device provides a sound stimulus for tinnitus treatment to a user who is a tinnitus patient on a unit time basis, and includes: a controller; and a recording medium in which a treatment program is stored. The treatment program is executed by the controller to perform: analogizing one or both of a RI effect curve and a TL decrease curve for tinnitus treatment sound provided to the user; generating the tinnitus treatment sound based on the one or both of the RI effect curve and the TL decrease curve which is analogized; and presenting the tinnitus treatment sound generated to the user via a sound presentation unit on the unit time basis to provide the sound stimulus to the user.

13 Claims, 25 Drawing Sheets

(56) References Cited

OTHER PUBLICATIONS

Atkinson, R., and Shiffrin, R. (1968), "Human Memory: A Proposed System and its Control Processes", Psychol Learn Motiv, 89-195, doi:10.1016/s0079-7421(08)60422-3.
Nishihara, M., Inui, K., Motomura, E., Otsuru, N., Ushida, T., and Kakigi, R., (2011), "Auditory N1 as a change-related automatic response", Neurosci. Res. 71, 145-148.
Yamashiro, K., Inui, K., Otsuru, N., Kida, T., and Kakigi, R., (2009), "Automatic auditory off-response in humans: An meg study", Eur J Neurosci. 30: 125-131.
English translation of Written Opinion of the International Searching Authority issued on Jan. 22, 2019 in International (PCT) Application No. PCT/JP2018/042361.
Jastreboff, PJ, "Phantom Auditory Perception (Tinnitus): Mechanisms of Generation and Perception", Neuroscience Research, the Japan Neuroscience Society, Aug. 1990, vol. 8, issue 4, pp. 221-254.
Langguth, B., Kreuzer, PM., Kleinjung, T., and De Ridder, D., (2013), "Tinnitus: causes and clinical management", Lancet Neurol, 12(9): 920-930, doi: 10.1016/S1474-4422(13)70160-1.
Sedley, W., Friston, K.J., Gander, P.E., Kumar, S., and Griffiths, T.D., (2016), "An Integrative Tinnitus Model Based on Sensory Precision", Trends Neurosci. 39(12):799-812. doi: 10.1016.
Henry, J.A., Roberts, L.E., Caspary, D.M., Theodoroff, S.M., and Salvi, R.J., (2014), "Underlying Mechanisms of Tinnitus: Review and Clinical Implications", J Am Acad Audiol, 25(1): 5-22; quiz 126, doi: 10.3766/jaaa.25.1.2.
Heller, M.F., and Bergman, M., (1953), "VII Tinnitus Aurium in Normally Hearing Persons", Ann Otol. 62: 73 -83.
Tucker, D.A., Phillips, S.L., Ruth, R. A., Clayton, W.A., Royster, E., and Todd, A.D., (2005), "The Effect of Silence on Tinnitus Perception", Otolaryngol Head Neck Surg. 132(1):20-24.
Del Bo, L., Forti, S., Ambrosetti, U., Costanzo, S., Mauro, D., Ugazio, G., Langguth, B., and Mancuso, A., (2008), "Tinnitus aurium in persons with normal hearing: 55 years later", Otolaryngol Head Neck Surg. 139(3): 391-4, doi:10.1016/j.otohns.2008.06.019.
Roberts, L.E., Moffat, G., and Bosnyak, D.J., (2006), "Residual Inhibition Functions in Relation to Tinnitus Spectra and Auditory Threshold Shift", Acta Otolaryngol Suppl. 556:27-33.
Adjamian, P., Sereda, M., Zobay, O., Hall, D. A., and Palmer, A. R., (2012), "Neuromagnetic Indicators of Tinnitus and Tinnitus Masking in Patients with and without Hearing Loss", J Assoc Res Otolaryngol. 13:; 715-731, doi:10.1007/s10162-012-0340-5.
Schaette, R., and McAlpine, D., (2011), "Tinnitus with a Normal Audiogram: Physiological Evidence for Hidden Hearing Loss and Computational Model", J. Neurosci. 31: 13452-13457.
Weisz, N., Hartmann, T., Dohrmann, K., Schlee, W., and Norena, A., (2006), "High-frequency tinnitus without hearing loss does not mean absence of deafferentation", Hear. Res. 222: 108-114.
Zhang, Y., Cheng, B., Koerner, T.K., Schlauch, R.S., Tanaka, K., Kawakatsu, M., Nemoto, I., and Imada, T., (2016), "Perceptual Temporal Asymmetry Associated with Distinct ON and OFF Responses to Time-Varying Sounds with Rising versus Falling Intensity: A Magnetoencephalography Study", Brain Sci. 6(3): 27.
Vaz Pato, M., and Jones, S.J. (1999), "Cortical processing of complex tone stimuli: mismatch negativity at the end of a period of rapid pitch modulation", Cogn Brain Res. 7:295-306.
Sams, M., Hari, R., Rif, J., and Knuutila, J. (1993), "The Human Auditory Sensory Memory Trace Persists about 10 sec: Neuromagnetic Evidence", J Cogn Neurosci. 5(3):363-70.
Winkler, I., and Cowan, N., (2005), "From Sensory to Long-Term Memory: Evidence from Auditory Memory Reactivation Studies", Exp Psychol. 52: 3-20.
Nishihara, M., Inui, K., Morita, T., Kodaira, M., Mochizuki H, et al., (2014), "Echoic Memory: Investigation of its Temporal Resolution by Auditory Offset Cortical Responses", PLoS ONE 9(8): e106553, doi:10.1371/journal.pone.0106553.
Crowder, R. G., and Morton, J. (1969), "Precategorical acoustic storage (PAS)", Percept Psychophys. 5, 365-373, doi:10.3758/bf03210660.
Watkins, MJ., and Todres, A.K., (1980), "Suffix Effects Manifest and Concealed: Further Evidence for a 20-Second Echo", J Verbal Learning Verbal Behav, 19(1):46-53.
Friston, K., Kilner, J., and Harrison, L., (2006), "A free energy principle for the brain", J Physiol Paris. 100:70-87.
Terry, A.M., Jones, D.M., Davis, B.R., and Slater, R., (1983), "Parametric studies of tinnitus masking and residual inhibition", Br. J. Audiol, 17:245-256 (English abstract only).
Vernon, J.A., and Meikle, M.B., (2003), "Tinnitus: clinical measurement", Otolaryngol ClinN Am. 36:293-305.
Roberts, L.E., Moffat, G., Baumann, M., Ward, L.M., and Bosnyak, D.J., (2008), "Residual Inhibition Functions Overlap Tinnitus Spectra and the Region of Auditory Threshold Shift", J Assoc Res Otolaryngol. 9(4): 417-435.
Galazyuk, A.V., Voytenko, S.V., and Longenecker, R.J., (2017), "Long-Lasting forward Suppression of Spontaneous Firing in Auditory Neurons: Implication to the Residual Inhibition of Tinnitus", J Assoc Res Otolaryngol. 18: 343-353.

* cited by examiner

FIG. 13A

130

| Course - Scene | Time length hh:mm:ss | Sound No. -A | Sound No. -B | Reproduction level-A | Reproduction level-B |
|---|---|---|---|---|---|
| 01-00 | 00:01:00 | 16 | 30 | 30 | 30 |
| 01-01 | 00:02:00 | 17 | 21 | 30 | 30 |
| ⋮ | | | | | |
| 01-15 | 00:01:30 | 00 | 27 | 25 | 25 |
| 02-00 | 00:02:00 | 20 | 02 | 30 | 50 |
| ⋮ | | | | | |

FIG. 14

120

| Sound No. | Category | Name |
|---|---|---|
| 00 | N/A | Silence |
| 01 | Noise wide | White noise |
| 02 | Noise wide | Pink noise |
| ⋮ | ⋮ | ⋮ |
| 06 | Noise wide | Gray noise |
| 07 | Noise narrow | 125-Hz band |
| ⋮ | ⋮ | ⋮ |
| 16 | Noise narrow | 6000-Hz band |
| 17 | Noise narrow | 8000-Hz band |
| ⋮ | ⋮ | ⋮ |
| 21 | Tone | La 6 |
| 22 | Tone | La# 6 |
| ⋮ | ⋮ | ⋮ |
| 43 | Tone | Do 8 |
| 44 | Environmental nisoe | Raindrops |
| 45 | Environmental nisoe | Beach |
| ⋮ | ⋮ | ⋮ |
| 59 | Environmental nisoe | Autumn insect 2 |
| 60 | Environmental nisoe | Crowds |
| 61 | User 1 | Synthetic sound - High |
| 62 | User 2 | Synthetic sound - Low |
| 63 | User 3 | User sound recording 2017 |

FIG. 15

150

| YYYYMMDD-No.-A/B | Time hh:mm:ss | Sound material data No. | Frequency | Reproduction level | Load score |
|---|---|---|---|---|---|
| 20170301-01- A | 00:01:00 | 16 | 5800-6200 | 30 | 30 |
| 20170301-01-B | 00:01:00 | 30 | 2793 | 30 | 30 |
| 20170301-02-A | 00:02:00 | 17 | 7800-8200 | 30 | 60 |
| 20170301-02-B | 00:02:00 | 21 | 1760 | 30 | 60 |
| ⋮ | ⋮ | ⋮ | ⋮ | ⋮ | ⋮ |

FIG. 16

140

| Plan No. | Frequency | Load score |
|---|---|---|
| 01-01 | 5800-6200 | 6000 |
| 01-02 | 2793 | 5000 |
| 01-03 | 7800-8200 | 2000 |
| 01-04 | 1760 | 1500 |
| ⋮ | ⋮ | ⋮ |

| | | 125 | 250 | 500 | 1000 | 1000 | 4000 | 8000 |
|---|---|---|---|---|---|---|---|---|
| R | A | 10 | 5 | 10 | 10 | 15 | 10 | 15 |
| | B | | 0 | 0 | 5 | 10 | 10 | |
| L | A | 20 | 25 | 30 | 40 | 50 | 65 | 75 |
| | B | | 20 | 25 | 40 | 50 | 60 | |

TINNITUS TREATMENT DEVICE AND RECORDING MEDIUM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This application is a reissue application of U.S. Pat. No. 11,228,854.*

TECHNICAL FIELD

The present invention relates to a device that outputs a treatment sound that is used for suppressing or alleviating tinnitus that a patient perceives and the like.

BACKGROUND ART

Tinnitus is one kind of perception of a sound for which there is no corresponding external sound as a sound source. Tinnitus is said to affect from several percent to 15 percent of the general population. There is still no method to objectively examine tinnitus, and the cause is also unclear.

The pitches, tones and sizes of tinnitus sounds that patients perceive are various. It is known that although patients who complain of tinnitus symptoms have a hearing impairment in a frequency band around the pitch of the tinnitus sound, patients with hearing impairments do not necessarily perceive tinnitus sounds.

In recent years it has been reported that the use of a hearing aid is effective as a method for suppressing tinnitus. Further, as a conventional method for suppressing tinnitus other than by use of a hearing aid, a method employing masking (masker therapy) that uses a device that generates a sound (mask sound) that masks tinnitus may be mentioned. It has been reported that masker therapy has a certain effect with respect to suppressing tinnitus, albeit temporarily.

Further, the auditory neurophysiological theory presented by Jastreboff is a representative theory regarding the mechanism of generation of tinnitus (see NPL 1). In addition, based on this theory, there is a treatment therapy tinnitus that is called "Tinnitus Retraining Therapy" (hereinafter, referred to by the acronym "TRT") (see NPL 2). TRT is a training therapy which aims at adaptation to tinnitus, and which includes providing counseling to the patient and having the patient listen to sounds.

CITATION LIST

Patent Literature

[PTL 1] Japanese Unexamined Patent Application Publication (Translation of PCT Application) No. 2011-505915

[PTL 2] U.S. Pat. No. 2,605,361

Non Patent Literature

[NPL 1] Jastreboff P J, "Phantom auditory perception (tinnitus): mechanisms of generation and perception", Neuroscience Research, the Japan Neuroscience Society, August 1990, vol. 8, issue 4, pp. 221-254

[NPL 2] Langguth, B., Kreuzer, P M., Kleinjung, T., and De Ridder, D. (2013). Tinnitus: causes and clinical management. Lancet Neurol. 12(9): 920-930. doi: 10.1016/S1474-4422(13)70160-1

[NPL 3] Sedley, W., Friston, K. J., Gander, P. E., Kumar, S., and Griffiths, T. D. (2016). An Integrative Tinnitus Model Based on Sensory Precision. Trends Neurosci. 39(12): 799-812. doi: 10.1016.

[NPL 4] Henry, J. A., Roberts, L. E., Caspary, D. M., Theodoroff, S. M., and Salvi, R. J. (2014). Underlying mechanisms of tinnitus: review and clinical implications. J Am Acad Audiol. 25(1): 5-22; quiz 126. doi: 10.3766/jaaa.25.1.2.

[NPL 5] Heller, M. F., and Bergman, M. (1953). VII Tinnitus Aurium in Normally Hearing Persons. Ann Otol. 62: 73-83.

[NPL 6] Tucker, D. A., Phillips, S. L., Ruth, R. A., Clayton, W. A., Royster, E., and Todd, A. D. (2005). The effect of silence on tinnitus perception. Otolaryngol Head Neck Surg. 132(1):20-24.

[NPL 7] Del Bo, L., Forti, S., Ambrosetti, U., Costanzo, S., Mauro, D., Ugazio, G., Langguth, B., and Mancuso, A. (2008). Tinnitus aurium in persons with normal hearing: 55 years later. Otolaryngol Head Neck Surg. 139(3): 391-4. doi: 10.1016/j.otohns.2008.06.019.

[NPL 8] Roberts, L. E., Moffat, G., and Bosnyak, D. J. (2006). Residual inhibition functions in relation to tinnitus spectra and auditory threshold shift. Acta Otolaryngol Suppl. 556:27-33.

[NPL 9] Adjamian, P., Sereda, M., Zobay, O., Hall, D. A., and Palmer, A. R. (2012). Neuromagnetic Indicators of Tinnitus and Tinnitus Masking in Patients with and without Hearing Loss. J Assoc Res Otolaryngol. 13: 715-731. doi:10.1007/s10162-012-0340-5.

[NPL 10] Schaette, R., and McAlpine, D. (2011). Tinnitus with a normal audiogram: physiological evidence for hidden hearing loss and computational model. J. Neurosci. 31: 13452-13457.

[NPL 11] Weisz, N., Hartmann, T., Dohrmann, K., Schlee, W., and Norena, A. (2006). High-frequency tinnitus without hearing loss does not mean absence of deafferentation. Hear. Res. 222: 108-114.

[NPL 12] Zhang, Y., Cheng, B., Koerner, T. K., Schlauch, R. S., Tanaka, K., Kawakatsu, M., Nemoto, I., and Imada, T. (2016). Perceptual temporal asymmetry associated with distinct on and off responses to time-varying sounds with rising versus falling intensity: a magnetoencephalography study. Brain Sci. 6(3): 27.

[NPL 13] Inui, K., Urakawa, T., Yamashiro, K., Otsuru, N., and Nishihara, M. (2010). Non-linear laws of echoic memory and auditory change detection in humans. BMC Neuroscience. 11: 80.

[NPL 14] Vaz Pato, M., and Jones, S. J. (1999). Cortical processing of complex tone stimuli: mismatch negativity at the end of a period of rapid pitch modulation. Cogn Brain Res. 7:295-306.

[NPL 15] Atkinson, R., and Shiffrin, R. (1968). Human Memory: A Proposed System and its Control Processes. Psychol Learn Motiv. 89-195. doi:10.1016/50079-7421(08)60422-3.

[NPL 16] Sams, M., Hari, R., Rif, J., and Knuutila, J. (1993). The Human Auditory Sensory Memory Trace Persists about 10 sec: Neuromagnetic Evidence. J Cogn Neurosci. 5(3):363-70.

[NPL 17] Winkler, I., and Cowan, N. (2005). From sensory to long-term memory: Evidence from auditory memory reactivation studies. Exp Psychol. 52: 3-20.

[NPL 18] Nishihara, M., Inui, K., Morita, T., Kodaira, M., Mochizuki H, et al. (2014). Echoic Memory: Investigation of Its Temporal Resolution by Auditory Offset Cortical Responses. PLoS ONE 9(8): e106553. doi:10.1371/journal.pone.0106553.

[NPL 19] Nishihara, M., Inui, K., Motomura, E., Otsuru, N., Ushida, T., and Kakigi, R. (2011). Auditory N1 as a change-related automatic response. Neurosci. Res. 71, 145-148.

[NPL 20] Yamashiro, K., Inui, K., Otsuru, N., Kida, T., and Kakigi, R. (2009). Automatic auditory off-response in humans: An meg study. Eur J Neurosci. 30: 125-131.

[NPL 21] Crowder, R. G., and Morton, J. (1969). Precategorical acoustic storage (PAS). Percept Psychophys. 5, 365-373. doi:10.3758/bf03210660.

[NPL 22] Watkins, M J., and Todres, A. K. (1980). Suffix effects manifest and concealed: Further evidence for a 20-second echo. J Verbal Learning Verbal Behay. 19(1): 46-53.

[NPL 23] Friston. K., Kilner, J., and Harrison, L. (2006). A free energyprinciple for the brain. J Physiol Paris. 100: 70-87.

[NPL 24] Terry, A., Jones, D. M., Davis, B. R., and Slater, R. (1983). Parametric studies of tinnitus masking and residual inhibition. Br. J. Audiol. 17:245-256

[NPL 25] Vernon, J. A., and Meikle, M. B. (2003). Tinnitus: clinical measurement. Otolaryngol Clin N Am. 36:293-305.

[NPL 26] Roberts, L. E., Moffat, G., Baumann, M., Ward, L. M., and Bosnyak, D. J. (2008). Residual inhibition functions overlap tinnitus spectra and the region of auditory threshold shift. J Assoc Res Otolaryngol. 9(4): 417-435.

[NPL 27] Galazyuk, A. V., Voytenko, S. V., and Longenecker, R. J. (2017). Long-Lasting forward Suppression of Spontaneous Firing in Auditory Neurons: Implication to the Residual Inhibition of Tinnitus. J Assoc Res Otolaryngol. 18: 343-353.

SUMMARY OF INVENTION

Technical Problem

Even though the effectiveness of suppressing tinnitus by use of hearing aids has been recognized, the specific mechanism by which an effect is achieved is not clear. The volume of tinnitus cannot be controlled by design.

Further, the mechanism by which masker therapy brings about an effect is unclear, and the theory has not been established. Consequently, protocols relating to application of masker therapy, such as characteristics and usage times of mask sounds have not been established. Therefore, it is hard to say that this method is being applied with the necessary optimization for each patient.

PTL 1 discloses that an effect comparable to masker therapy is obtained by presenting "optimized sounds that are softer than the tinnitus and have different pitch qualities than the tinnitus" rather than sounds that mask tinnitus. However, this is not a proposal that is based on a novel view relating to the mechanism of a tinnitus suppression effect, similarly to the conventional masker therapy.

Further, no specific verification has been carried out with respect to the theory of NPL 1. The theory described in NPL 1 is that the patient's own strong awareness (alertness) with respect to the tinnitus amplifies the sound, however a sound that is cause of the tinnitus is not actually measured, and the tinnitus sound does not decrease in TRT. The purpose of counseling the patient and having the patient listen to sounds in TRT is to weaken the strong awareness that the patient has with respect to a specific sound. However, because there is no simulation regarding the adequacy of the frequency distribution of treatment sounds that patients are made to listen to in TRT, it is not possible to select and use an appropriate treatment sound based on the effectiveness for each patient. Consequently, depending on the patient, it may be difficult to find an appropriate treatment sound, and the burden on the therapist such as a doctor and the patient increases, and there are many cases where an appropriate treatment sound cannot be found and the treatment ends unsuccessfully.

A device which the inventor of the present application considers is necessary for the treatment of tinnitus is a device which controls tinnitus sounds based on a mechanism by which tinnitus is recognized and rules which are deduced from data based on measurement which will be described later. The present invention provides a tinnitus treatment device and the like that, by systematically and efficiently finding a treatment sound suitable for suppressing or alleviating tinnitus of each patient (hereunder, also referred to simply as "treatment of tinnitus"), reduces the burden of the therapist and the patient, and also presents the treatment sound.

Solution to Problem

A tinnitus treatment device in accordance with an aspect of the present invention provides a sound stimulus for tinnitus treatment to a user who is a tinnitus patient on a unit time basis, and includes: a controller; and a recording medium in which a treatment program is stored, wherein the treatment program is executed by the controller to perform: analogizing one or both of a residual inhibition (RI) effect curve and a TL decrease curve for tinnitus treatment sound provided to the user; generating the tinnitus treatment sound based on the one or both of the RI effect curve and the TL decrease curve which is analogized; and presenting the tinnitus treatment sound generated to the user via a sound presentation unit on the unit time basis to provide the sound stimulus to the user.

In accordance with another aspect of the present invention, a non-transitory computer-readable recording medium is embodied with a tinnitus treatment program. The tinnitus treatment program controls a tinnitus treatment device, the tinnitus treatment device including a controller and being a device that provides a sound stimulus for tinnitus treatment to a user who is a tinnitus patient on a unit time basis. The treatment program is executed by the controller to perform: analogizing one or both of a residual inhibition (RI) effect curve and a TL decrease curve for tinnitus treatment sound provided to the user; generating the tinnitus treatment sound based on the one or both of the RI effect curve and the TL decrease curve which is analogized; and presenting the tinnitus treatment sound generated to the user via a sound presentation unit on the unit time basis to provide the sound stimulus to the user.

It should be noted that general or specific aspects of the present invention may be implemented to a system, an integrated circuit, a computer program, a computer-readable recording medium such as a Compact Disc-Read Only Memory (CD-ROM), or any given combination thereof.

Advantageous Effects of Invention

The tinnitus treatment device according to the present invention reduces the burden of a therapist and a patient in finding a treatment sound suitable for suppressing or alleviating the tinnitus of each patient, and presents a treatment sound that is found.

BRIEF DESCRIPTION OF DRAWINGS

FIG. 13A is a diagram illustrating an example of the data structure of course data used in the tinnitus treatment device according to the embodiment.

FIG. 14 is a diagram illustrating an example of a sound material list used in the tinnitus treatment device according to the embodiment.

FIG. 15 is a diagram illustrating an example of the data structure of treatment history data used in the tinnitus treatment device according to the embodiment.

FIG. 16 is a diagram illustrating an example of the data structure of treatment plan data used in the tinnitus treatment device according to the embodiment.

Figure 1:
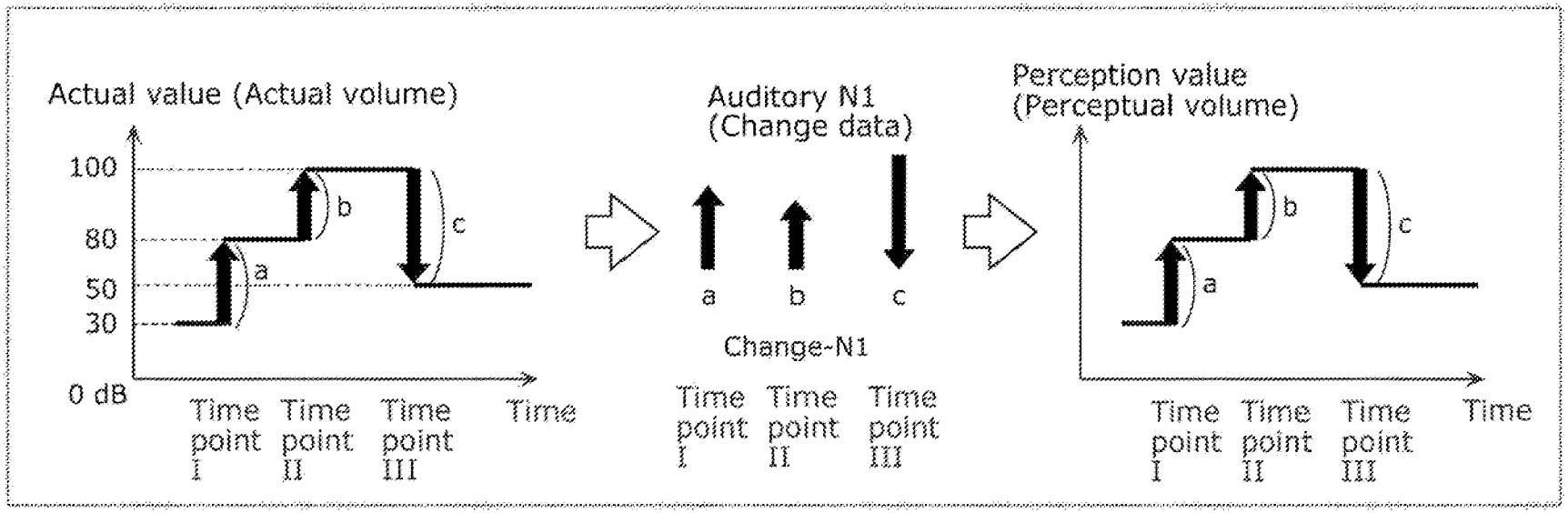
FIG. 1 is a schematic diagram illustrating an example of perception of sound by integrating changes in a sound, for describing a finding that serves as a basis for the invention according to the present application.

DESCRIPTION OF EMBODIMENTS (Findings that Form the Basis of the Present Invention)

The inventor has devised a new theory relating to the mechanism of tinnitus generation. It is believed that this theory is consistent with the phenomena confirmed in the past and with phenomena observed in treatment that we have performed using the tinnitus treatment device according to the present invention.

Whilst the present application does not investigate the truth of this theory, at least in the treatment performed according to this theory, and also in the conventional findings, it is shown that tinnitus can be favorably controlled by providing an appropriate kind of sound at an appropriate magnitude for an appropriate time as a sound load to a patient.

An outline of the mechanism of tinnitus generation and the theory serving as the basis of tinnitus treatment using the tinnitus treatment device according to the present invention based on this mechanism are described hereunder.

Introduction

Tinnitus is the perception of a sound in the absence of a corresponding external auditory stimulus. Most individuals experience transient tinnitus, whereas chronic tinnitus is present in about 10%-15% of the population (NPL 2). Although many explanatory models of tinnitus have been proposed to date, few adequately and comprehensively explain the features that characterize the phantom characteristic (NPL 3). Almost all models hypothesize that a change in neural activity or an auditory cortex structural abnormality is the main driver of tinnitus (NPL 4).

However, the neural changes proposed by these models would require several days to develop (NPL 4), which is in stark contrast with some of the temporal features of tinnitus.

1. Tinnitus can suddenly occur within a few minutes after a person is placed in a completely silent environment, only to subside as soon as the person returns to a normal environment (NPL 5, 6, 7).

2. Tinnitus is almost immediately attenuated (generally within one minute) by the presentation of a masker sound. When the masker sound is removed, the tinnitus percept returns to pre-masker levels within a few minutes (NPL 8, 9, 10, 11).

Here, we introduce a novel mechanistic model of tinnitus, the perception update (PU) model. This model is an information-processing model based on a data compression technology commonly used for compressing music and image files, called differential pulse code modulation (also referred to as "differential PCM"; see PTL 2), and indicates that tinnitus is caused by a data compression error. The model further postulates that the auditory cortex recognizes a sound input by comparing the sound input to the input of the previous moment, and thus acts as a detector of input changes. In this model, the auditory N1, a prominent electromagnetic response that is elicited approximately 100 ms after the onset and offset of a discrete tone or after an alteration of a continuous tone (NPL 12), signals a change detection process within the auditory cortex. Indeed, recent studies have revealed that the auditory N1 detects change by comparing the information of a preceding stimulus with that of a subsequent stimulus (NPL 13).

[Auditory N1 as a Change Detector]

As stated above, the auditory N1 is a prominent cerebral cortical response to both the start (the on-response: On-N1) and the end (the off-response: Off-N1) of an auditory stimulus (NPL 12). There is also a possibility that an auditory N1 can be elicited by infrequent changes in pitch or timbre of a continuous complex tone (Change-N1; see NPL 14).

Sensory memory has been defined as the shortest memory in the multi-store memory model (NPL 15), and is believed (NPL 18) to last in the range of 10 seconds (NPL 16) to 15 seconds (NPL 17). Furthermore, sensory memory is attention-independent, and is specific to the sensory system.

Nishihara et al. (NPL 19) concluded that ON-N1 and Change-N1 are both generated by the same neural mechanism and are part of the change detection system that is based on sensory memory. Furthermore, they showed that whereas a Change-N1 response is elicited by any change in acoustic stimulation, ON-N1 is a response elicited by a change from preceding silence. Finally, Yamashiro et al. (NPL 20) reported that, similarly to ON-N1, OFF-N1 is also a response based on sensory memory systems, and that both ON-N1 and OFF-N1 can be considered as subtypes of Change-N1. In light of these findings regarding Change-N1, ON-N1 and OFF-N1 are now also considered responses that signal a detected change in auditory stimulation.

[Sound Perception Achieved by Integrating Sound Change]

To illustrate how the integration of sound input change leads to perception, FIG. 1 shows an example of a discrete tone burst (for example, 6,000 Hz) arriving in the auditory system. A marked change in neuronal firing in the auditory cortex takes place at the start and end of the stimulus. In a case where the brain derives sound intensity (volume) based on a change in the auditory input, it is necessary to integrate the actual value of change.

The driving hypothesis behind the perception update (PU) model is that sound perception is continuously updated within the auditory system by determining at any given moment the relative change in input from the immediately preceding moment, rather than being obtained by determining the absolute sound parameters.

For example, let us consider a situation where an auditory stimulus is initially at 30 dB, and thereafter increases to 80 dB at a time point I, is then further increased to 100 dB at a time point II, only to finally decrease to 50 dB at a time point III. The auditory cortex receives new information that is distinct from previously received information from the inner ear at the time point I, the time point II, and the time point III. At each of these time points, an auditory N1 is elicited by the sound change. The PU model proposes that the auditory N1 signals the magnitude of change (+50, +20, and −50), as opposed to the absolute magnitude (for example, sound level) of the stimulus. Consequently, the auditory system achieves perception by integrating the relative values provided by the auditory N1.

Figure 2A:
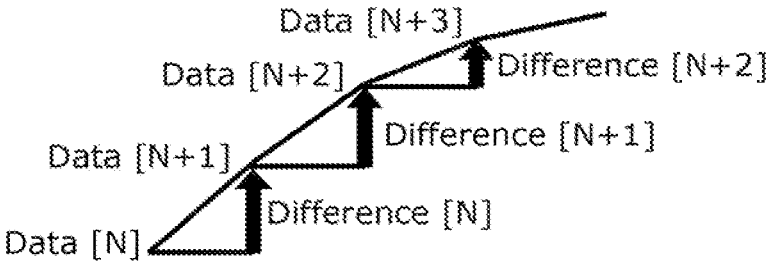
FIG. 2A is a diagram illustrating an example of differential PCM (Pulse Code Modulation).
Figure 2B:
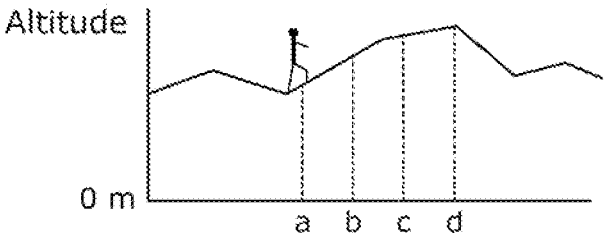
FIG. 2B is a schematic diagram illustrating differential PCM that shows an example of ridge height measurement, for describing a finding that serves as a basis for the invention according to the present application.
Figure 2C:
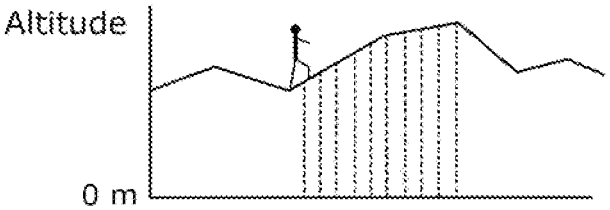
FIG. 2C is a schematic diagram which, similarly, with respect to ridge height measurement, illustrates that as the measurement interval decreases, the height difference between each interval point decreases.

The PU model is analogous to a data compression/decompression technology called "differential pulse code modulation (differential PCM)" (PTL 2). Differential PCM is used for processing data that is correlated with adjacent data, such as for the processing of voice and image files. Referring to FIG. 2A, the next data point (Data [n+1]) is derived by adding an altitude difference (difference [n]) relative to the current data point (Data [n]). FIG. 2B illustrates how differential PCM works using an example of a mountain climber walking along a path running along a ridge. The altitude (relative position with respect to sea level) at each point on the path can be acquired by: (1) directly measuring the height at each point, or (2) measuring the height above sea level only at the point "a", and then calculating the difference in elevation (relative to the previous point) at each of the other points. If we want to acquire the altitude at very short intervals (for example, every 10 m) on the path (FIG. 2C), because there are many measurement points compared to the case illustrated in FIG. 2B, the size of the data relating to altitude for the entire path increases. Here, the shorter the interval between adjacent points, the smaller the difference in height between the points. This difference can be represented with a fewer number of bits, that is, a smaller data size. Accordingly, when using the method of (2), an increase in the data size can be suppressed in comparison to the method of (1).

This precisely shows how data compression methods would treat the data to reduce the information by using fewer bits than the original information, which is essential for processing large amounts of continuous information at very fine intervals. We propose here that the auditory system processes sound information by a similar method. In practice, data compression and decompression calculations are achieved using mathematical integration and differential equations to deal with continuously changing values. However, for simplicity, these stepwise changes can be evaluated by simple addition and subtraction.

[Arbitrariness of Sound Perception Results from Uncertainty within the Auditory System]

Figure 3:
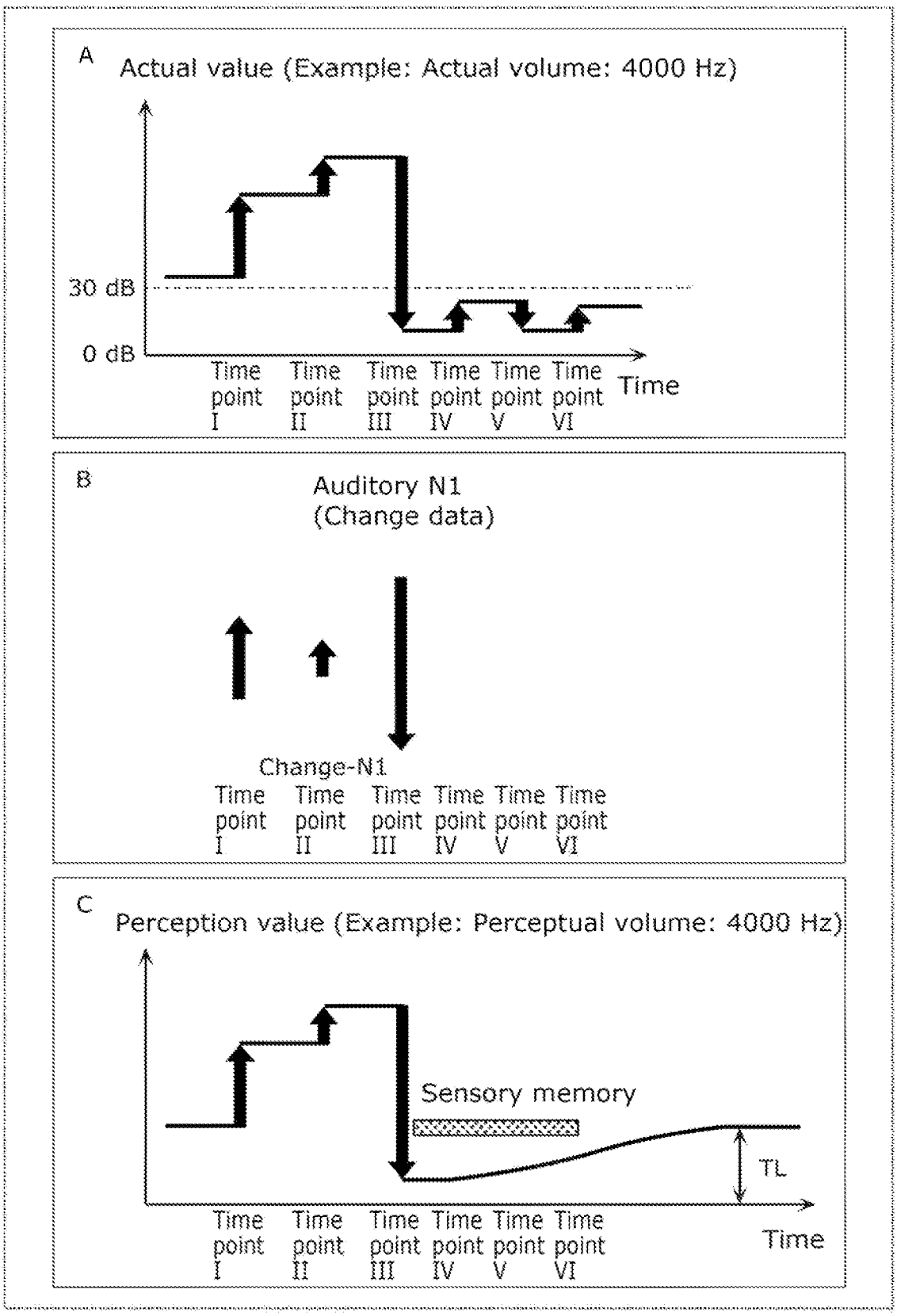
FIG. 3 is a schematic diagram for describing the process of tinnitus generation in patients in a Perception Update (PU) model that serves as a basis for the invention according to the present application.

The PU model posits that the auditory system constantly updates its perception state based on changes in the acoustic signal, and that perception is updated when an auditory N1 is evoked. In the absence of an N1 response, the PU model proposes that perception can be maintained for the duration of sensory memory. Given the existence of multiple short-term storage systems exist in the brain, it may be possible for the auditory system to maintain perception for a short duration without requiring an update in the sensory input. Such systems include sensory memory and echoic memory, which are believed to last between 10 seconds (NPL 16) and 15 seconds (NPL 17), although some authors have argued that these storage systems may preserve the sensory trace for even longer periods (NPL 16, NPL 21, and NPL 22). However, if inner damage inhibits the ability of the auditory system to perceive a specific sound frequency, the auditory system may not be able to properly detect the volume of sounds presented at that same frequency. FIG. 3 (panels A and B) illustrates this situation, where the auditory system cannot reliably detect sound changes that produce maximal volumes of 30 dB or less. More specifically, panel A illustrates a situation where sound changes cannot be detected below a certain threshold in the case of inner ear damage, and panel B illustrates the absence of N1 responses for sub-threshold acoustic changes (time point IV, time point V, and time point VI). In the case of tinnitus (panel C), the PU model suggests that once the acoustic stimulation drops below the lower limit for a given frequency for a duration period longer than the length of sensory memory, perception cannot be maintained and becomes uncertain. Since sensory memory gradually decreases accompanying the cessation of a stimulus, and lasts approximately 10 seconds (NPL 16), the influence thereof on sensory perception also gradually decreases and ends approximately 10 seconds after the cessation of the stimulus. In such cases, when the period of sensory memory is exceeded, a perceptual drift takes place and perception becomes uncertain, and this can lead to a phantom percept. Perception can become arbitrary as it can take various different values, including those that produce such phantom percepts.

In such a case, the brain infers perception based on a theory such as predictive coding, and therefore the perception value reaches the predicted value. A person who, for some reason, has acquired a tendency to reach a predicted value that deviates from a normal environmental sound perceives tinnitus. Such a predicted value is defined as TL. That is, tinnitus is an event where an arbitrary perception led to an incorrect predicted value TL.

[Acute Phase and Chronic Phase of Tinnitus]

Figure 4:
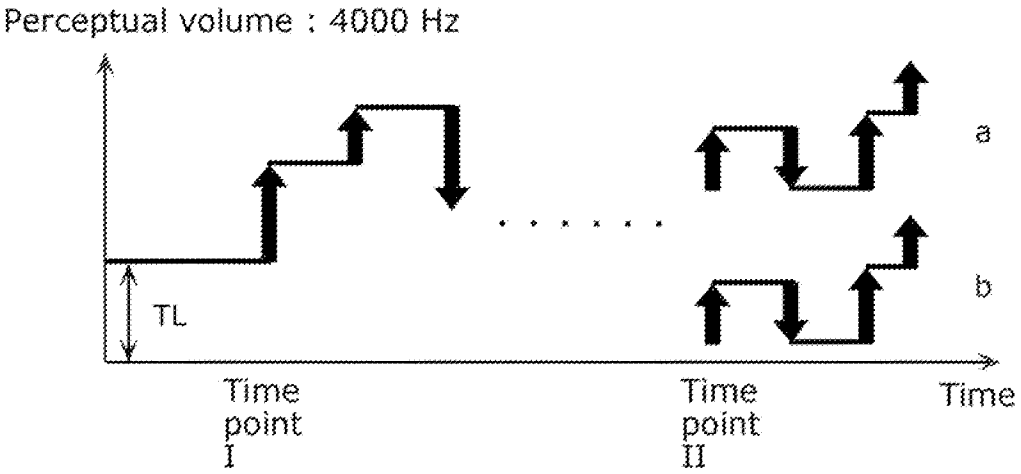
FIG. 4 is a schematic diagram illustrating a difference between an acute phase and a chronic phase of tinnitus by the presence/absence of correction of predicted values of tinnitus.

When the perception value fluctuates owing to lack of input of a sound change in a person with either normal hearing or early acute tinnitus, tinnitus may not emerge because the value is within the usual range of environmental noise. However, when the perception value reaches a magnitude exceeding that of the environment, there is a possibility that tinnitus will emerge. The basic assumption of the PU model is that tinnitus is a perception of an erroneous prediction value, TL. In a quiet environment, the perception value is equal to TL (=tinnitus volume) for individuals with tinnitus. When an external sound input is present, the perception value is equal to the volume of the external input added to TL. This concept is illustrated in FIG. 4. When a sound change input arrives at time point I, by definition of the PU model the next perception value is calculated by adding the change input to the current perception value (TL). Subsequent calculations of perception values are continued based on the current value from the baseline added to the TL. That is, the TL behaves like an integer constant in a mathematical integration. Therefore, external input is perceived in addition to the tinnitus percept at the corresponding frequency band (for example, 4000 Hz).

In addition, let us also consider a case where external input continues afterward. When there is sufficient external input, TL is not necessarily fixed at a wrong value all the time. Rather, the wrong TL may be corrected to ensure internal consistency (see FIG. 4, b). In NPL 23 it is described that in the theory of free energy, the brain uses generalized coordinates to optimize predictive coding. Generalized coordinates are common concepts in physics, and are typically used for assessing object position and momentum. For example, when viewing a landscape from a moving train, it is recognized that the position of the landscape is fixed though the viewpoint changes. The impression that the viewpoint changes according to the movement is what the brain learned about the causal structure of the world. We believe that the concept of moving coordinates also applies to the perception of sound volume. This is because changing the integral constant TL is analogous to moving coordinates. In the case of differential PCM, the possibility that errors due to such integral constants frequently occur is high, and there should be a method to deal with such errors. Individuals with normal hearing can perceive sounds of low amplitude. Even if the TL is initially inaccurate, the brain can still correct the TL to an appropriate value by calculating the occurrence probability of such low-volume sounds in a normal environment. By correcting the TL value to a value of zero, the tinnitus percept thus becomes zero. This precise situation corresponds to a state of acute tinnitus.

On the other hand, once the perception value has shifted for a long time, it is difficult to correct the TL any further, even with sufficient external input. Since the perception of phantom percepts had been the basis of everyday life, clues to the normal world have been lost. People who are hearing impaired lack information for obtaining accurate recognition. In such case, TL is not corrected and remains wrong. The sound change inputs are calculated in a state shifted upward by TL (as if TL is an integral constant), and external sounds are perceived together with tinnitus (FIG. 4, a). Thereafter, if there is no further change in the external sound input, the predicted value and the perception value will again drift toward the TL. The predicted value of this chronic tinnitus patient tends toward TL when drifting. We have defined TL as such a phenomenon.

This concept of TL is similar to the predicted value of tinnitus in the Sedley model (NPL 3). Both theories argue that tinnitus is the result of incorrect predictions within the framework of predictive coding. In the PU model, predicted values are defined for each frequency, where the perception is expressed as a sum of the TL and the value of the external sound for a given frequency. On the other hand, in the Sedley model, the predicted value of the tinnitus percept is defined separately. However, both models can still adequately account for the emergence of tinnitus.

SUMMARY

1. The predicted value represents a perceived sound volume averaged over several seconds for a given frequency. Each frequency has its own corresponding predicted value.
2. TL is one of the predicted values, and in particular corresponds to the tinnitus frequency band.
3. Tinnitus is perception of an erroneous TL (predicted value).

(1) Typical Situation

Tinnitus volume (TV)=TL.

[When there is no external sound: silence]:

Perception value=TL (=tinnitus volume): only tinnitus is heard.

[When there is external sound]:

Perception value=TL (=tinnitus volume)+external sound volume: external sound and tinnitus are heard.

(2) In Cases of Residual Inhibition

Tinnitus volume<TL: described later (see panel C of FIG. 5).

4. Acute tinnitus: TL is variable and can be corrected to 0.
5. Chronic tinnitus:

(1) TL is nearly constant and cannot be corrected to 0. (Gradually fluctuates with long-time masker.)

(2) The perception value is calculated by changes of external sound, with TL being the reference value (integral constant).

(3) When the perception value drifts, it heads toward the TL.

[Mechanism of Residual Inhibition (RI) According to PU Model]

Residual inhibition (RI) refers to the phenomenon where the tinnitus percept remains suppressed following the offset of an appropriate masking stimulus, and typically lasts for a period on the order of tens of seconds (NPL 24, 25). RI is optimally induced by a masking sound with an intensity greater than the minimum intensity required to mask the tinnitus (NPL 26). Galazyuk et al. (NPL 27), using in vivo extracellular recording in awake mice, found that about 40% of spontaneous activity of inferior colliculus neurons exhibited forward suppression after sound offset. They showed the duration of this suppression increased with sound duration and lasted about 40 seconds following a 30 second stimulus offset, and concluded that these characteristics are similar to the psychoacoustic properties of RI. We show that the RI phenomenon can also be explained by the PU model. Consequently, we believe that both theories are not mutually exclusive and can coexist.

Figure 5:
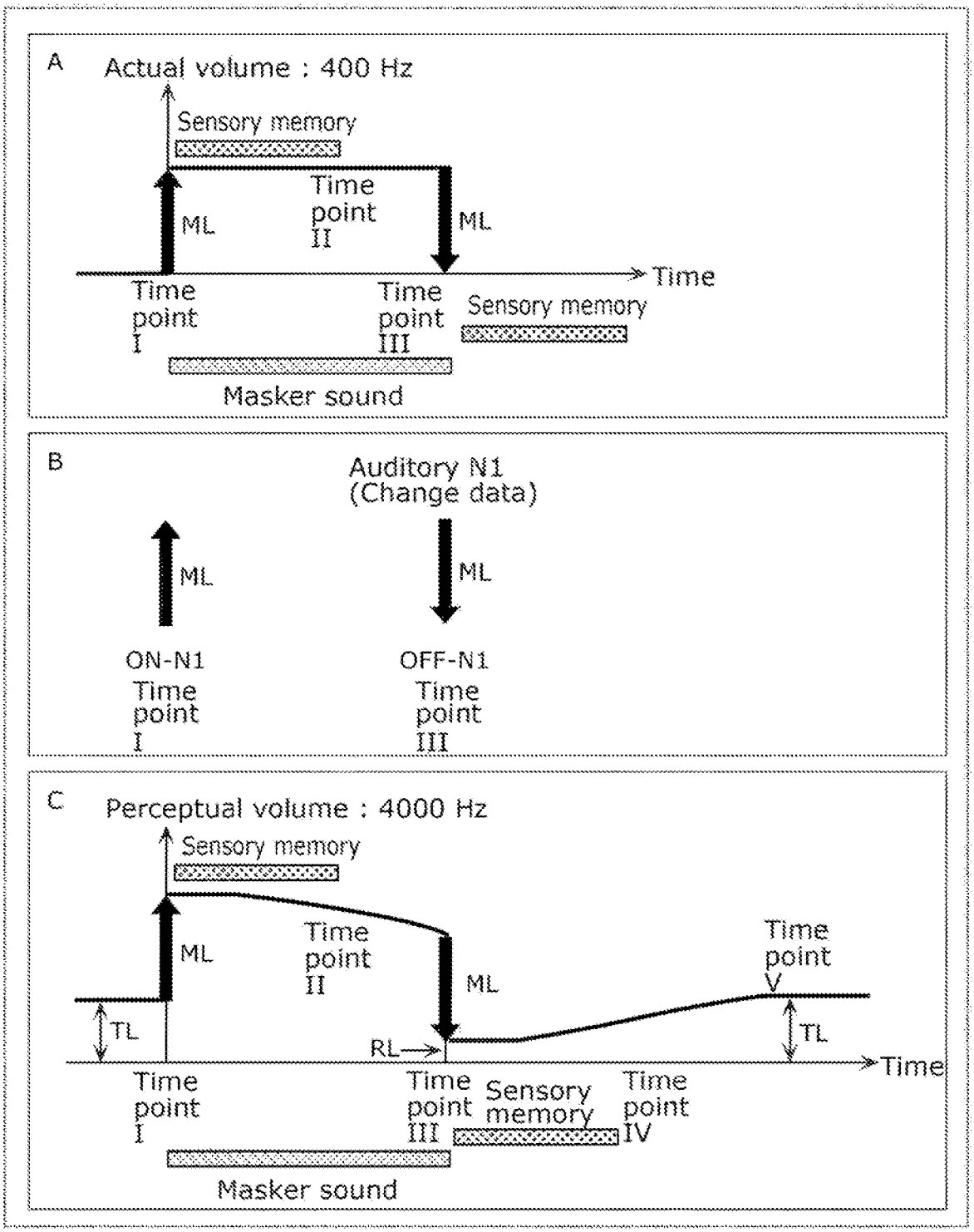
FIG. 5 is a schematic diagram for describing the principle of Residual Inhibition (RI), in accordance with a hypothesis of the process of tinnitus generation in patients.

FIG. 5 illustrates how the RI of a chronic patient is explained by the PU model. Panel A illustrates the influence of the volume of a masker sound on the actual volume. Panel B illustrates the auditory N1 response evoked by the masker sound. Panel C illustrates the progress of the perceptual volume of a tinnitus patient brought about by a masker sound. In this specific example, a 4000 Hz masker is presented. Although this example is specific to a sound of 4000 Hz, this phenomenon is thought to occur simultaneously in parallel for all frequencies. Prior to time point I, the perception value is equal to the TL in the usual state and is equal to the predicted value (TL) of this chronic patient. At time point I, the masker loudness (ML) is added, thus resulting in a perception value equal to TL+ML. The model stipulates that when the masker is presented for a longer duration than that of sensory memory, the perception value (TL+ML) cannot be maintained. As previously highlighted, when the perception value becomes uncertain and drifts, a force directed towards TL acts. However, because perception is updated owing to the fluctuation of the masker sound, the perceptual drift is limited and consequently the perception value does not reach TL.

When the masker sound stops, the change (subtraction) in input decreases the perception value and causes a temporary inhibition of the tinnitus percept, and thus the tinnitus perception value becomes RL. Here, the tinnitus perception value immediately after residual inhibition (RI) is defined as RL. However, when the unchanged state continues longer than the limit of sensory memory (time IV), it becomes impossible to maintain perception. The perception value then shifts from the RL to the TL. The validity of the PU model is confirmed by examining the tinnitus volume (TL), the masker loudness (ML), the masker duration (from time point I to time point III: masker sound presentation time), the RI depth (TL−RL: the rate of decrease in the tinnitus volume after the cessation of the masker), and the RI duration (time point I-time point V). The results of previous studies, as described later in this section, are approximately consistent with this hypothesis. For RI to occur, the masker loudness must exceed the tinnitus volume, and the masker duration should preferably last 10 seconds or more. As the masker duration increases, the RI duration is increased as a (logarithmic) function of the masker duration, approaches an asymptote after approximately one minute, and then reaches a plateau (NPL 24). This relationship between masker loudness, duration, and RI duration is also in good agreement with the predictions made by the PU: once the masker duration exceeds the duration of 10 seconds, which corresponds to the duration of sensory memory, the perceived sound intensity gradually decreases. The longer the masker duration (from time point I to time point III), the longer the period from time point II to time point III, and thus the greater the decrease in perceived sound intensity before time point III. This results in a greater RI depth and a longer RI duration. The RI duration is limited by the maximal RI depth, which implies that increasing the masker duration beyond a certain point will not have an additional effect on RI. The RI duration is usually approximately a few tens of seconds, but it is not uncommon for the RI to last more than a few minutes (NPL 25).

This can be explained as follows. Even in a very quiet environment, several sounds can still be heard (for example, breathing, rubbing of clothes). Depending on the hearing ability of each individual, these low magnitude inputs may or may not lead to perceptual updates within the auditory system. If these sounds remain below the hearing threshold of an individual, without perceptual updates, the perception value will drift smoothly toward the TL. Conversely, if the sounds are heard, the perceptual drift toward the TL is delayed. In other words, when individuals with better hearing are in noisy environments, the reappearance of tinnitus is delayed. Both Roberts et al. and Terry et al. indicated that RI depth is proportional to the masker loudness provided that the tinnitus is completely masked (NPL 26, NPL 24). It was also shown that RI depth depends on the center frequency of the masking sound (NPL 26). Furthermore, the best RI depth is obtained when using a masking sound with the frequency region where the hearing impairment is present (NPL 8). These studies indicated that tinnitus and its RI depend on processes that span the frequency region of the hearing impairment, and not on mechanisms that produce cortical representations for sound frequencies at the edge of the hearing impairment area (audiometric edge). Based on these facts, the authors suggested that the neuron synchronization model can explain the RI mechanisms more adequately than the Tonotopic Reorganization Model (NPL 26). The PU model can also explain the fact that the RI depth is theoretically maximized by a masker that matches the frequency of the hearing impairment. This is derived by combining the relationship between the tinnitus and the hearing impairment (see FIG. 3) and the relationship between the tinnitus and the masking sound (see FIG. 5) at each frequency. Finally, the PU model can be further validated by examining the relationship between RI depth and duration in tinnitus patients by parametrically manipulating the presented masker loudness and frequency.

[Validation of the Perception Update (PU) Model]

Regular perception updates reduce the likelihood of potential perceptual drifts.

The PU model assumes that perceptual drifts will occur if there is no change in sound input. We can verify that the perceptual drift is delayed by promoting perception updates several times during the RI period. Specifically, we can experimentally confirm whether the RI effect changes within a period of no change.

[Experiment 1: After Masker Presentation (from Time Point III to Time Point V)]

Figure 6:
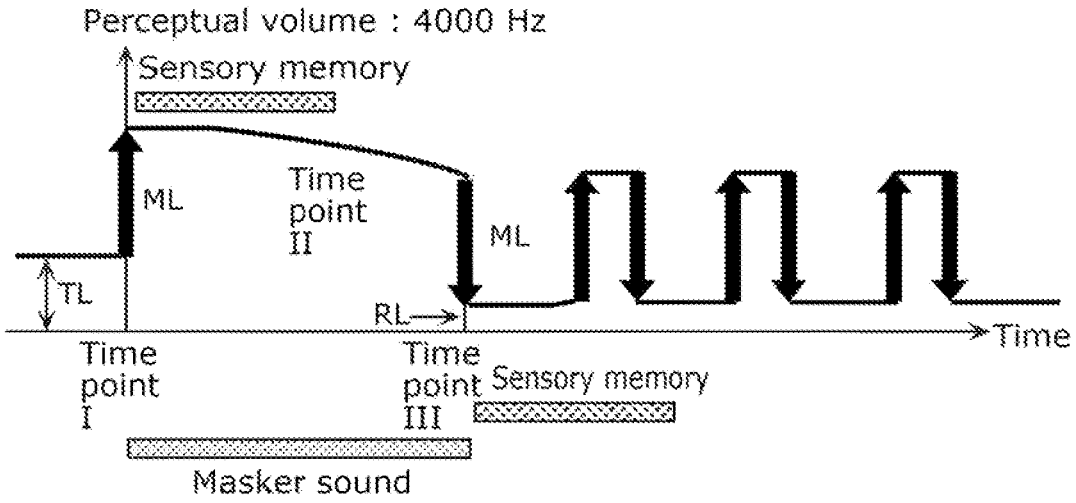
FIG. 6 is schematic diagram illustrating that, for tinnitus for which the volume was lowered once by RI or a long-time masker effect, in the subsequent recovery process, the tinnitus recovery process is delayed by inhibiting a perceptual drift by means of an efficient sound stimulus that gives rise to a perception update.

The perception value immediately after a masker presentation corresponds to RL, which is the value of the tinnitus reduced by the RI (FIG. 5). During the silent period after the masker presentation, there is no change in input and, consequently, perception is not updated. This leads to perceptual uncertainty and creates a perceptual drift. If a slight change in input is produced during this period, it should promote a perceptual update and reduce the drift. This can be achieved by presenting short click sounds in the same frequency band as the tinnitus after the masker presentation to investigate the time required for the tinnitus volume to return to TL. This concept is illustrated in FIG. 6. This should prove to be effective at reducing tinnitus because the rapid changes in volume will produce perceptual updating, which will in turn cause further delay in the tinnitus recovery time, even for a small number of presentations at a low volume. The influence of stable sound and noise on delay of the tinnitus recovery time will be smaller than the click sound of shorter duration. At the beginning of the experiment, it is necessary to identify the optimal conditions (type of masker sound, masker loudness, masker presentation time) that produces the best RI in an insulated room for each patient with chronic tinnitus. Presentation of the masker is repeated under the same conditions in the following measurements.

As a control condition, during the silence after the masker presentation, we propose to first investigate the shape of the recovery curve from RL to TL in silence. The RL is measured immediately after the presentation (0 minutes) using an inspector (a standard apparatus used for determining the tinnitus volume by presenting sounds with various volumes so that the patient can select the one with the volume closest to the volume of the tinnitus). For each measurement, the time from the end of the masker presentation to the measurement varies from one minute to 10 minutes in one-minute steps, and RL is measured each time. It should be noted that repeating the masker presentation itself produces a reduction in the tinnitus, so there is a limit to the number of measurements in one day. This procedure allows for the time pattern of the tinnitus volume recovery (for example, logarithmic, linear, or exponential) after the masker presentation to be ascertained. We hypothesize that this time curve will correspond to the perceptual drift from RL to TL as it is a composite measure of the decay speed of sensory memory and the speed of drift.

[Experiment 2: During Masker Presentation (from Time Point I to Time Point III) (FIG. 5)]

For this experiment, if sound inputs are provided during the presentation of the masker, perceptual updating takes place in the auditory system causing the drift to slow down and decreasing the RI effect. This can be achieved by adapting the masker sound so as to cause it to change rapidly with increasing and decreasing sound volume changes of 10 dB (FIG. 7B). Even if there is a second pulsating masker with an opposite polarity (increasing when the other is decreasing, and conversely decreasing when the other is increasing) and the total masker amount is the same, the RI effect will decrease because of perceptual updating.

Figure 7A:
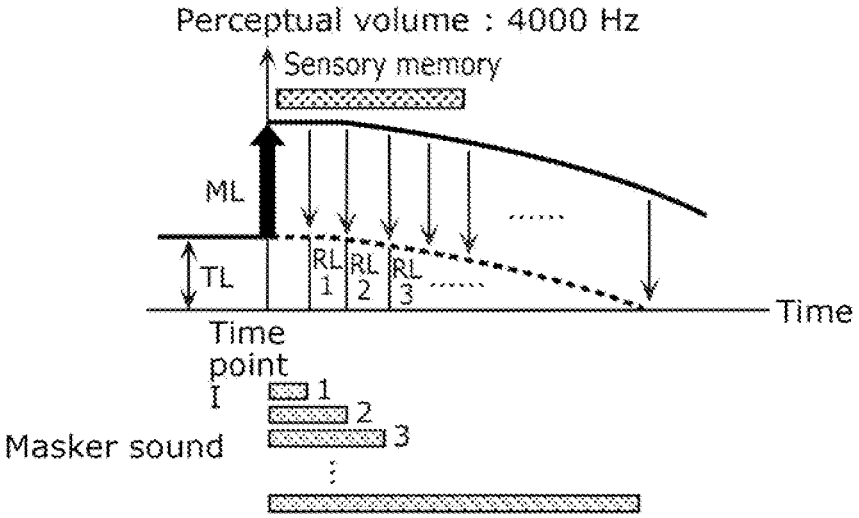
FIG. 7A is a schematic diagram illustrating an experiment designed to derive the time curve of the perceptual drift as a control.
Figure 7B:
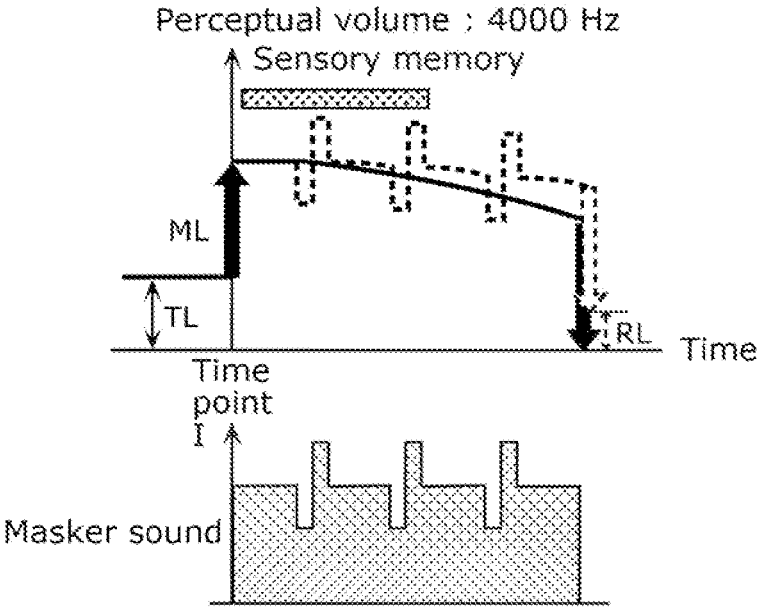
FIG. 7B is a schematic diagram illustrating an experiment in which the RI effect decreases due to a perception update, that is a comparative experiment in which the masker sound changes rapidly with increasing and decreasing sound volume changes of 10 dB.

For the comparison condition, we propose to use a usual masker sound and to derive the time curve of the perceptual drift of the overall volume (masker+tinnitus sound) (FIG. 7A). The tinnitus volume can be estimated before masker presentation by using an inspector. In each measurement, the masker sound presentation time differs in one-second steps from one second to 10 seconds or more, and RL is measured immediately after the end of the masker presentation. This time sequence of the RL obtained for different masker presentation times is thought to parallel the time sequence of the perceptual drift of the overall volume (masker+tinnitus sound). This allows us to infer the drift curve of the perception value during masker presentation. The inventor of the present application hypothesizes that it is a composite of the decay speed of sensory memory and the drift speed.

[Determination of RI (Residual Inhibition) Effect Curve]

A residual inhibition (RI) effect curve is determined by the following procedure.

A masker that causes RI for a certain specific patient is prepared.

Figure 8A:
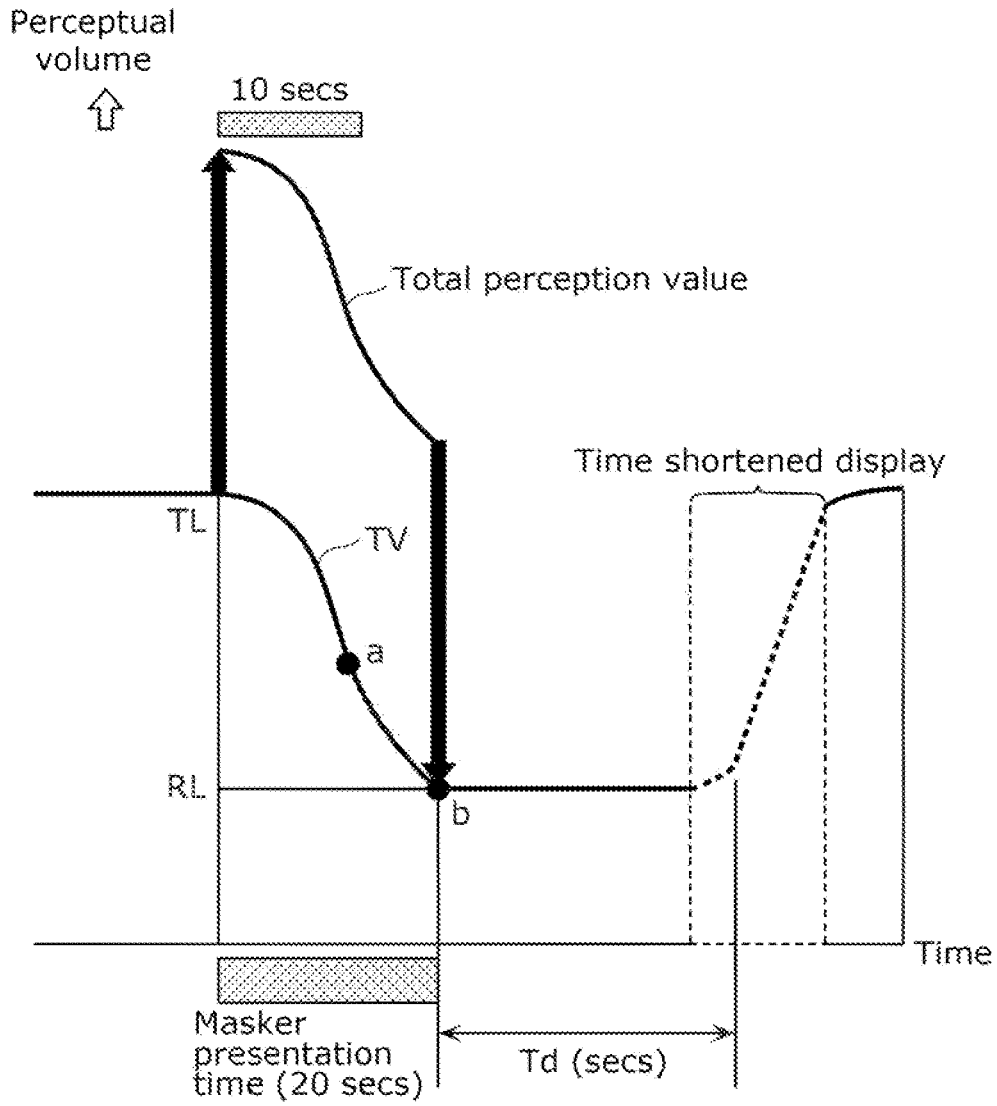
FIG. 8A is a diagram obtained by changing perception values by RI (RI effect curve) which illustrates an example in which the presentation time of the masker is 20 seconds, and which illustrates curves that estimate a total perception value that includes a masker sound, and a perception value (tinnitus volume) of only tinnitus that excludes the masker sound.

In FIG. 8A, an example is illustrated in which the masker presentation is 20 seconds and, before masker presentation, the patient has a perception value of TL that is the intrinsic value of the patient which is the volume of tinnitus, and illustrates the progress of the tinnitus volume (TV) thereafter.

The total perception value for which TV is added to the volume of the masker is also illustrated in parallel. The perception value (RL) after the masker ends is determined. A time in which TV begins to rise after the masker ends is defined as "Td".

Figure 8B:
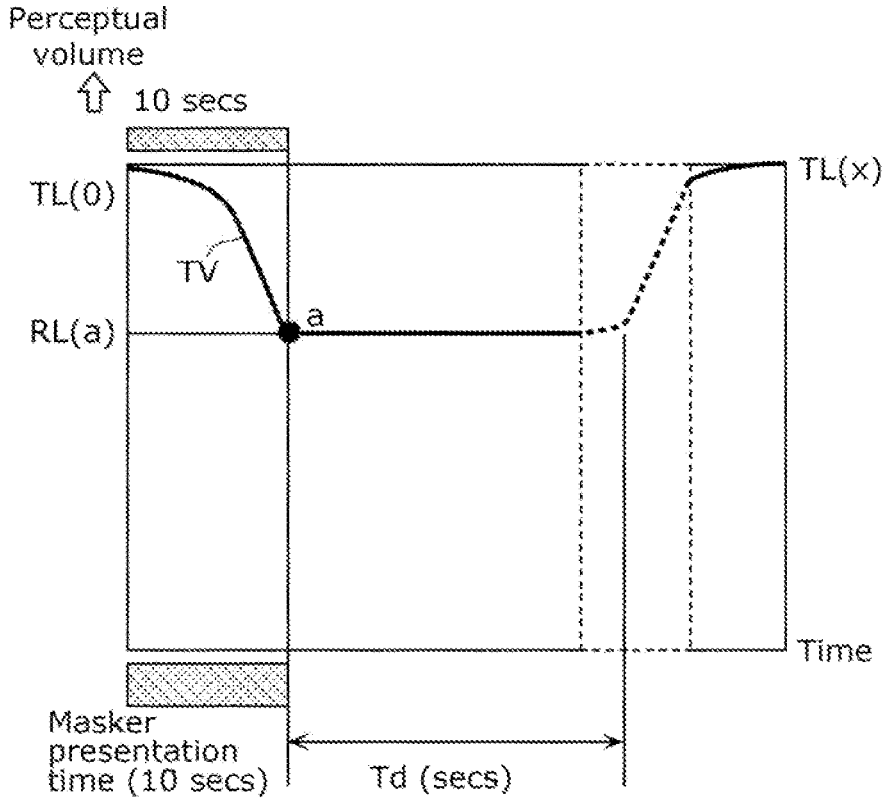
FIG. 8B is a diagram in which, similarly, a masker presentation time is 10 seconds, and only the tinnitus volume is displayed.
Figure 8C:
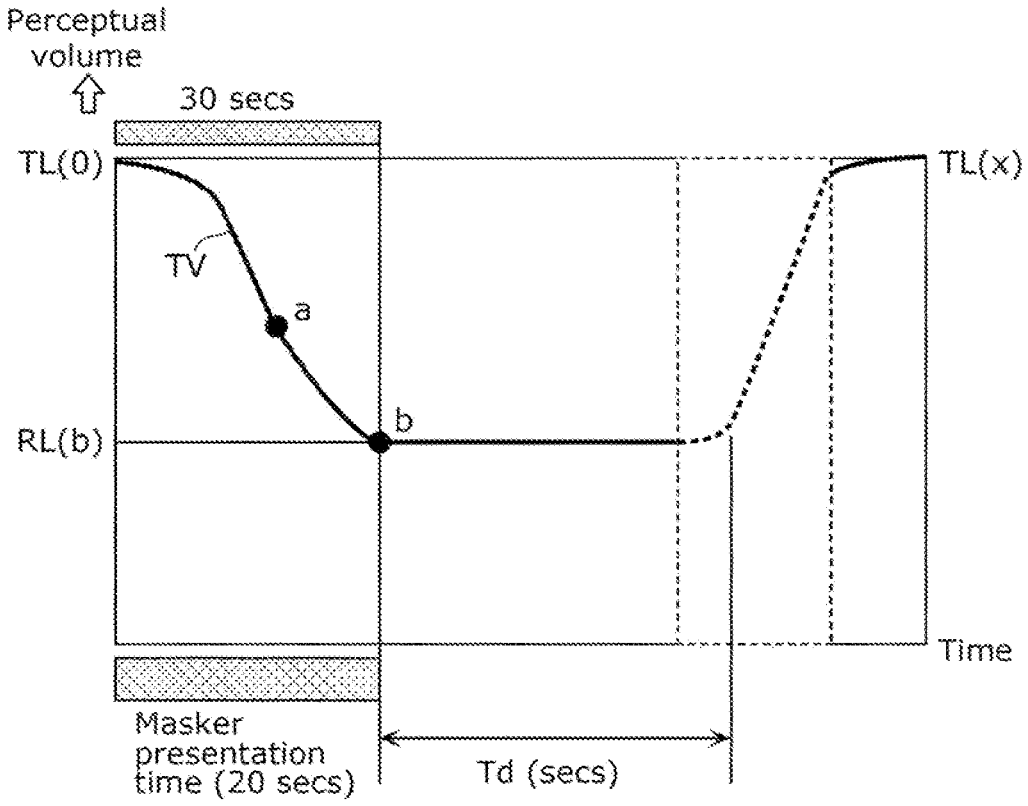
FIG. 8C is a diagram in which, similarly, the masker presentation time is 20 seconds, and only the tinnitus volume is displayed.

FIG. 8B and FIG. 8C illustrates states in which, for the same patient, maskers of the lengths of 20 or more kinds of sound of different lengths are presented every 10 secs in the manner of 10 secs, 20 secs, . . . 100 secs, . . . 200 secs. The sounds may also be in smaller units. In the case where the masker presentation time is 10 secs, if we assume that a curve as illustrated in FIG. 8B is obtained, RL(a) is the perception value after RI at 10 secs. The decrease in TV stops at a, and thereafter continues for a time while remaining at the value of TV=RL(a). The tinnitus volume (TV) increases after Td secs thereafter, and after 10 minutes the tinnitus volume recovers to the value of TL(x), and thereafter is assumed to be stable. Similarly, changes in the case of a masker presentation time of 20 secs are illustrated in FIG. 8C. In this case, after masker presentation a state in which TV=RL(b) continues for a while, and the value then gradually increases from Td secs, and recovers to the value TV=TL(x).

Figure 8D:
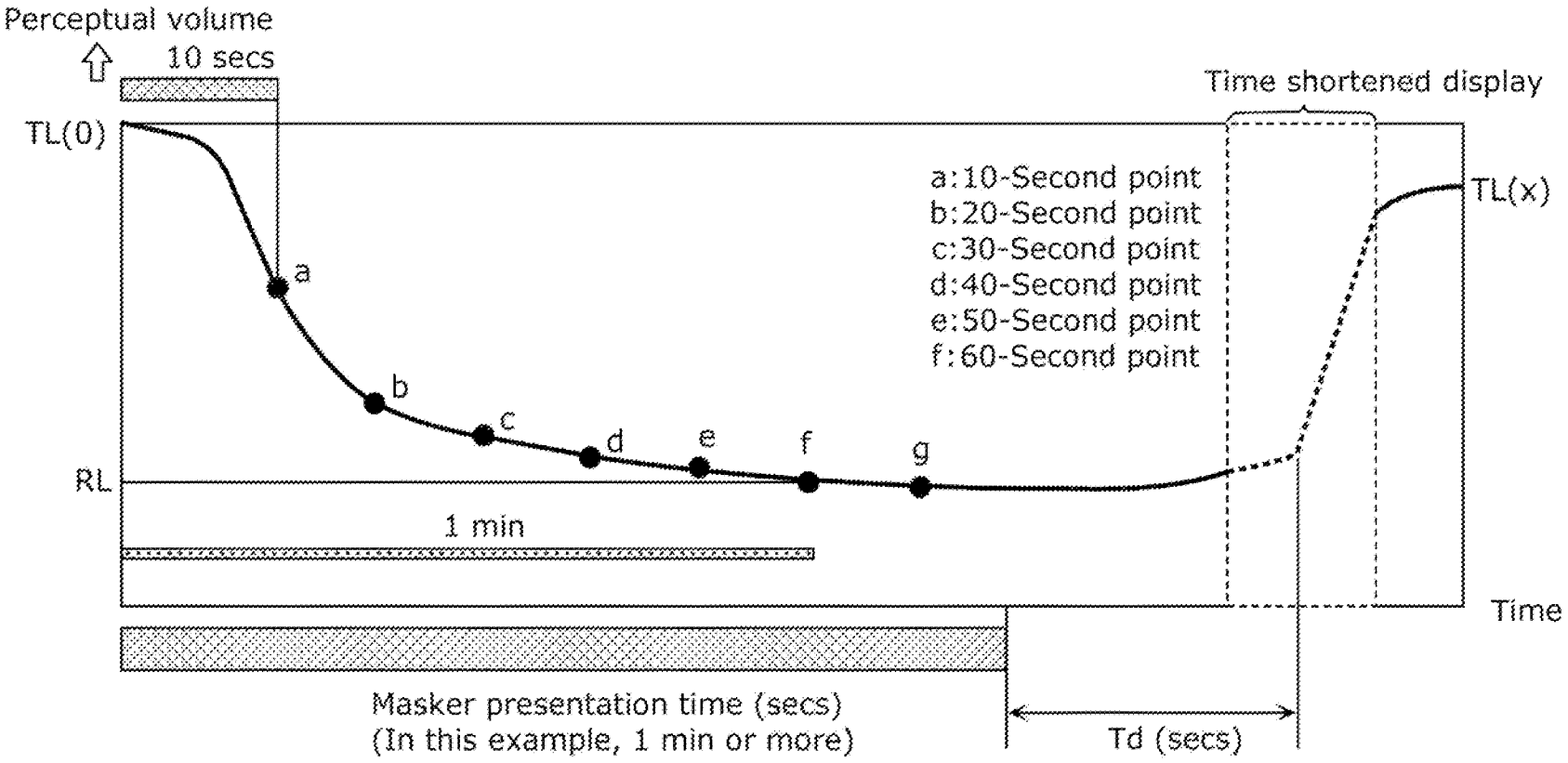
FIG. 8D is a diagram in which a curve of tinnitus volume is estimated in a case where the procedures of FIG. 8B and FIG. 8C are repeated and the masker presentation time is one minute or more.

The result of determining the values of RL at masker presentation times a, b, c, d, e, and f that are time points at 10-second intervals from 10 secs to 1 min in sequential order in this manner is illustrated in FIG. 8D, and by this means an RI effect curve is obtained. The decrease in RL is predicted to plateau from 1 min onwards as described in the theory of RI, and the change in RL thereafter is small.

In this RI effect curve, the perception value corresponding to tinnitus corresponds to a value that is decreased by perceptual drift. TL is the predicted value of tinnitus, and it is approximately constant for a short time, and TL(x) in FIG. 8B and FIG. 8C is approximately equal to TL(0) that is the initial value. Changes in TL cannot be disregarded in the case of a long time period, and this is an index of a long-time masker effect.

A curve of the RI effect of a specific masker sound with respect to a specific patient is obtained in this manner, and furthermore, measurement is performed to the extent possible for other sound sources or other patient groups (hearing impairment, tinnitus pitch and magnitude), and a data group is created by inference for others.

These curves were obtained against the background of the theory of the PU model by maintaining a balance between the speed of perceptual drift and the decay speed of sensory memory, and it has been verified that they can analogize a similar state together with a large amount of data.

Here, the RI effect curve will be defined. The term "RI effect curve" refers to a curve in which an RI effect is represented as the time course of tinnitus volume, and as illustrated in FIG. 8A to FIG. 8D, is the progress of a tinnitus volume that changes depending on a presented sound, and is a curve that represents progress from the start until the end of the presented sound and furthermore until the tinnitus volume returns to the original volume after the presented sound ends.

This kind of RI effect curve can be analogized based on the state of the hearing ability of the patient, the volume, frequency and tone of the presented sound, the changes over time in the aforementioned volume, frequency and tone, and the presentation time. In particular, the RI effect curve is analogized based on data from analogous patients and presented sounds.

Analogizing of an RI effect curve will now be described.

In FIG. 3 (there is no sound input), FIG. 5 (the sound input is constant, there is no sound input), FIG. 6 (the sound input is constant), and FIG. 7A (the sound input is constant) which are cases where there is no change in sound input, states are illustrated in which perceptual drift occurs and perception heads toward a constant value. As described in "Experiment 2: During masker presentation", it is hypothesized that this occurs due to a composite of the decay speed of sensory memory and the drift speed.

Although in this case the constant value that perception heads toward is the TL, for example, with respect to the perceptual drift during the masker presentation time in FIG. 5, a certain perception update occurs due to noise fluctuation of the masker and the perceptual drift is inhibited to some extent, and therefore does not completely reach TL. On the other hand, after the end of the masker in FIG. 5, if the silence continues, a perception update does not occur and perceptual drift is not inhibited, and therefore the perception reaches TL. In other words, the perception returns to the original tinnitus.

Due to such background, the curve of a perceptual drift has a certain tendency, and when an RI effect curve in a case where a specific sound source is presented to a specific patient at a specific volume for a specific period is taken as a typical example, a curve that approximates the RI effect curve in a case where another sound source is presented to another patient at another volume for another period can be obtained by (linearly or nonlinearly) scaling the typical curve along the ordinate axis (perception value) and the horizontal axis (time axis).

In fact, the present inventor was able to obtain many RI effect curves with minimal data by such kind of analogizing. [Method for Linearly or Non-Linearly Scaling in Either Time Axis or Volume Axis Direction to Analogize RI Effect Curve]

Figure 10A:
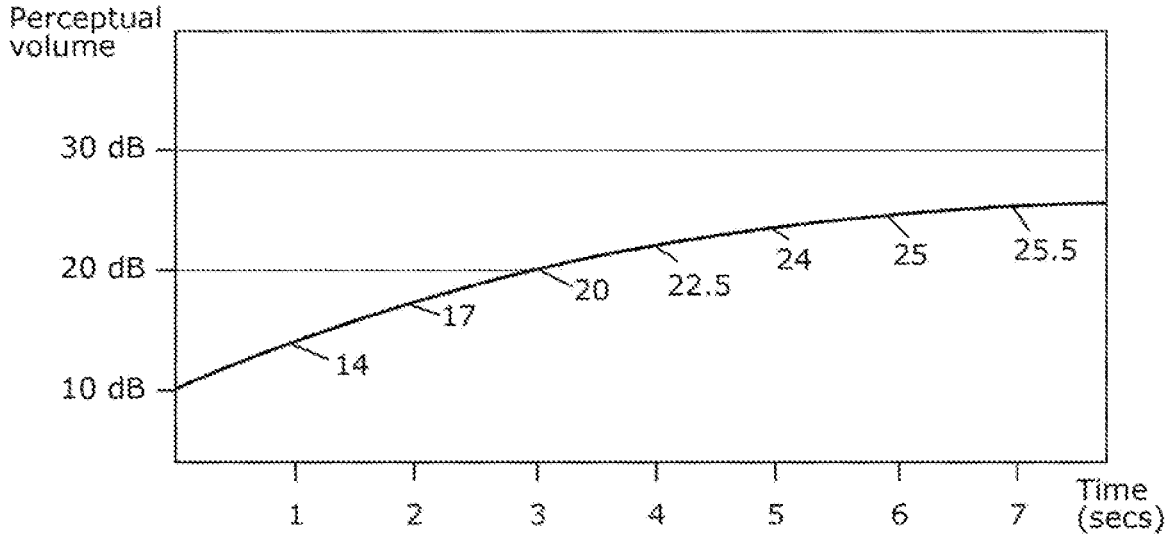
FIG. 10A is a diagram for describing analogizing of an RI effect curve, that illustrates an example of progress in which the tinnitus volume recovers to the initial tinnitus volume after a certain time period following tinnitus treatment sound presentation.

FIG. 10A is an example that illustrates a state in which the tinnitus volume recovers after a certain time has passed after masker sound presentation. The starting time point of the tinnitus volume recovery which is a time point that is Td seconds after the end of the masker presentation time illustrated in FIG. 8A, FIG. 8B, FIG. 8C, and FIG. 8D, corresponds to the starting point (0 secs) in FIG. 10A.

As shown in the following table, the relationship between time and tinnitus volume in the typical example was that the tinnitus volume was 10 dB at the time point of 0 seconds, and recovered to the original tinnitus volume of 25.5 dB after 8 seconds.

TABLE 1

| Time (Secs) | 0 | 1 | 2 | 4 | 5 | 6 | 7 | 8 |
|---|---|---|---|---|---|---|---|---|
| Perceptual volume (dB) | 10 | 14 | 17 | 20 | 22.5 | 24 | 25 | 25.5 |

In an example in which a different sound source T1 which was likely to cause a perception update was presented to a different patient P1 with comparatively good hearing ability, the tinnitus volume at the time point of 0 seconds was 0 dB, and recovered to the original tinnitus volume of 25.5 dB after a recovery time of 1,000 seconds.

Here, when each number of seconds on the time axis is applied to an exponential function, the resulting values are as follows: Exp (1)=2.7, Exp (2)=7.4, Exp (3)=20, Exp (4)=55, Exp (5)=148, and Exp (6)=403.

In addition, values obtained by applying a logarithmic function to perceptual volume y to convert into log(y)×30−70.5 are log (10)×30−70.5=0, log(14)×30−70.5=7.5, and thereafter similarly, log(17)×30−70.5=13.5, log(20)×30−70.5=19.5, log(22.5)×30−70.5=22.5, log(24)×30−70.5=24.6, log(25)×30−70.5=25.5, and log(25.5)×30−70.5=25.5.

Although this is an approximate calculation based on experience, but assuming that the flow of time is exponential, and also adjusting to the actual measured values, the value with respect to perceptual volume is a value corrected by −70 dB. The respective values are shown in the following table.

TABLE 2

| | | | | | | | | |
|---|---|---|---|---|---|---|---|---|
| After conversion (secs) | 1 | 2.7 | 7.4 | 20 | 55 | 148 | 403 | 1096 |
| After conversion (dB) | 0 | 7.5 | 13.5 | 19.5 | 22.5 | 24.6 | 25.5 | 25.5 |

Whilst this method of calculation is a rough method at the present time, it corresponded well to this example of the patient P1 and the sound source T1, including the intermediate progress. In addition, it was found that in the case of a sound source T2 with which it was somewhat difficult to cause a perception update, in an intermediate situation with respect to the typical example, by using this mathematical expression and adjusting the correction value, there were many cases where the intermediate progress applied well. Although this is merely one example that could be approximated with a mathematical formula, it will be developed by a detailed study of many examples in the future, and the present invention is not limited to this method of calculation. Further, even if analogy by means of a mathematical expression is not possible, analogy with a graph is also included as shown in an example that uses scaling for analogy of a TL decrease curve which is described later.

[Determination of TL Decrease Curve of Long-Time Masker Effect]

Although a masker effect (a state in which tinnitus is reduced for several hours due to a masker load of 2 to 3 hours) has already been reported, in the PU model this corresponds to a state in which the TL itself is reduced by presentation of the masker for a long time.

Here, a method for determining a TL decrease curve will be described specifically.

Figure 9A:
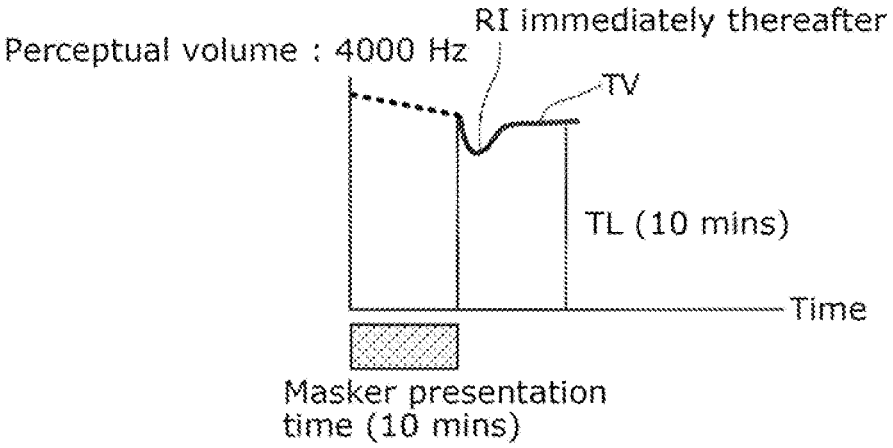
FIG. 9A is a schematic diagram illustrating the progress of the tinnitus volume as the result of sound stimuli being integrated in an example in which the masker presentation time is 10 minutes.
Figure 9B:
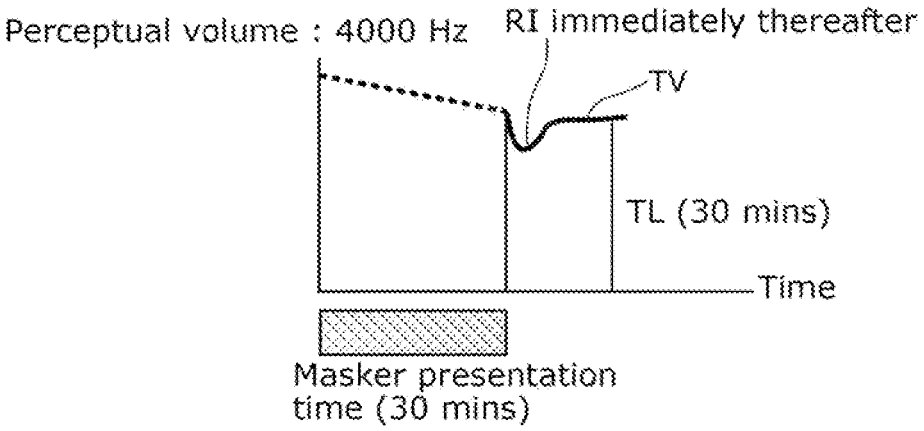
FIG. 9B is a schematic diagram that similarly illustrates the progress of the tinnitus volume in an example in which the masker presentation time is 30 minutes.
Figure 9C:
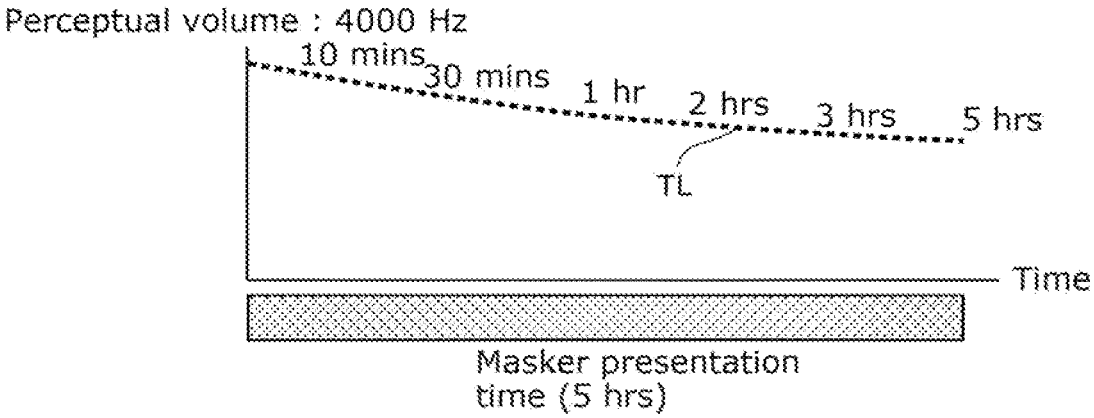
FIG. 9C is a schematic diagram illustrating a decrease curve of a predicted value of tinnitus in the case of a masker presentation time of 5 hours that is estimated using the values of tinnitus volume (=predicted value of tinnitus) obtained by repeating the procedures illustrated in FIG. 9A and FIG. 9B.

FIG. 9A illustrates, as one example, a state in which a masker sound that is 4000-Hz band noise is presented for 10 minutes, and the tinnitus volume (TV) is then determined in a stable state in which the influence of the immediately succeeding RI has disappeared. The total perceptual volume within the masker presentation time is the sum of the masker loudness ML and the tinnitus volume TV (ML+TV), and FIG. 9A shows only TV, the volume of the tinnitus that excludes ML among the total perceptual volume (ML+TV). Note that, it is assumed that the TV during masker presentation is equal to the TL. Immediately after the masker ends, the TV decreases because of the influence of RI. It is considered that the TV after the influence of RI disappears (for example, after 10 minutes) reflects the immediately preceding TL. That is, it is considered that the TL (10 minutes) shown in the drawing is approximately equal to the TV (=TL) when the masker presentation ends. Similarly, FIG. 9B illustrates an example where the TV at 30 minutes is determined, and this is taken as the TL after 30 minutes. A TL decrease curve created by determining the TL according to each masker presentation time in succession (for example, 10 minutes, 30 minutes, 1 hour, 2 hours, 3 hours, and 5 hours) in this manner is shown in FIG. 9C.

Thus, a specific masker sound is presented for different time periods (for example, 10 minutes, 30 minutes, . . . 1 hour, 3 hours, 5 hours) to a specific patient and the TL after each presentation is measured to create a TL decrease curve.

Measurement is also performed to the extent possible for other sound sources and other patient groups (hearing impairment, tinnitus pitch and magnitude), and a data group is created by inference for others.

By relying on a large number of examples, a TL decrease curve can be analogized with respect to each masker sound for each patient.

The term "TL decrease curve" will now be defined. The term "TL decrease curve" refers to curve that represents the time course of a decrease in TL that is caused mainly by a long-term sound stimulus, and each TL is measured as tinnitus volume that became a stable tinnitus volume for which the RI effect can be ignored after mainly around several minutes passed after the end of the presented sound as illustrated in FIG. 9A to FIG. 9C. In addition, the term "TL decrease curve" also includes a curve from when the sound stimulus ends until the TL is restored to the original TL.

This kind of TL decrease curve can be analogized based on the state of the hearing ability of the patient, the volume, frequency and tone of the presented sound, changes over time in the aforementioned volume, frequency and tone, and the presentation time. This kind of TL decrease curve can be analogized based on data from especially approximate patients and presented sound.

Analogizing of a TL decrease curve will now be described.

Figure 11A:
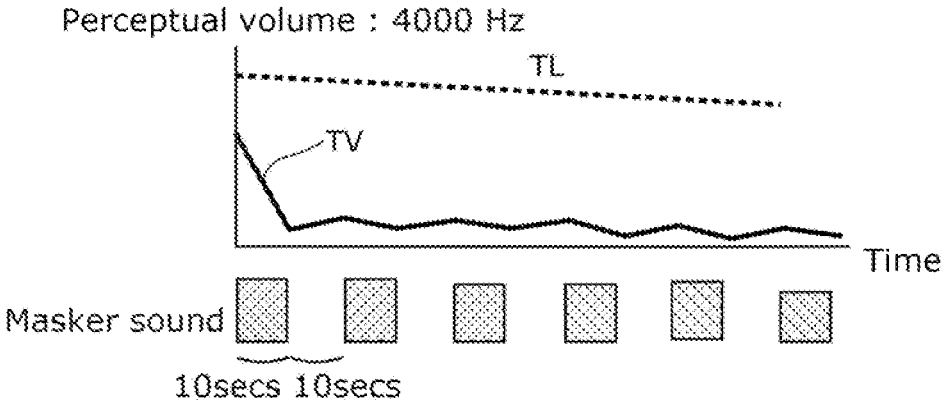
FIG. 11A is a diagram illustrating the progress of the tinnitus volume and a predicted value of tinnitus in a case where presentation of a masker sound for 10 seconds and silence for 10 seconds are repeated, in which the masker loudness decreases each time.
Figure 11B:
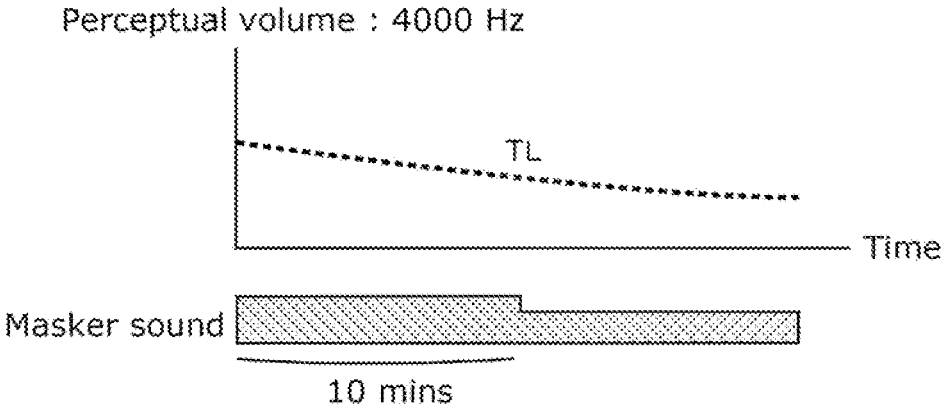
FIG. 11B is a diagram illustrating the progress of a predicted value of tinnitus in a case where a masker sound is presented for 10 minutes and thereafter the volume is slightly lowered.

As illustrated in FIG. 9A to FIG. 9C as well as FIG. 11A and FIG. 11B, it is observed that the TL decreases gradually as the presentation time of the presented sound increases. The TL is an erroneous prediction value, and when a TL decrease curve in a case where a specific sound source is presented at a specific volume for a specific period to a specific patient with a certain tendency is taken as a typical example, a curve that approximates the TL decrease curve in a case where another sound source is presented to another patient at another volume for another period can be obtained by (linearly or nonlinearly) scaling the typical curve along the ordinate axis (perception value axis) and the horizontal axis (time axis).

In fact, the present inventor was able to obtain many TL decrease curves with minimal data by such kind of analogizing.

[Method for Linearly or Non-Linearly Scaling in Either Time Axis or Volume Axis Direction to Analogize TL Decrease Curve]

Example 1 of TL Decrease Curve

TL decrease curve with respect to a 50 dB load of sound source A (4000-Hz band noise) and patient P1 (hearing distribution: high-frequency tapering from 3000 Hz, tinnitus: 4000 Hz, 40 dB) (extract)

TABLE 3

| | | | | | |
|---|---|---|---|---|---|
| Sound source presentation time | 10 mins | 30 mins | 1 hr | 2 hrs | 3 hrs |
| tinnitus volume immediately thereafter (TL) | 35 dB | 30 dB | 25 dB | 20 dB | 20 dB |
| Tinnitus recovery time | 20 mins | 40 mins | 2 hrs | 3 hrs | 3 hrs |

Example 2 of TL Decrease Curve

A TL decrease curve obtained with respect to a 70 dB load of sound source A when using the same sound source A and the same patient P1 as in Example 1 is shown in the following table.

TABLE 4

| | | | | | |
|---|---|---|---|---|---|
| Sound source presentation time | 10 mins | 30 mins | 1 hr | 2 hrs | 3 hrs |
| tinnitus volume immediately thereafter (TL) | 25 dB | 10 dB | 5 dB | 3 dB | 0 dB |

Figure 10B:
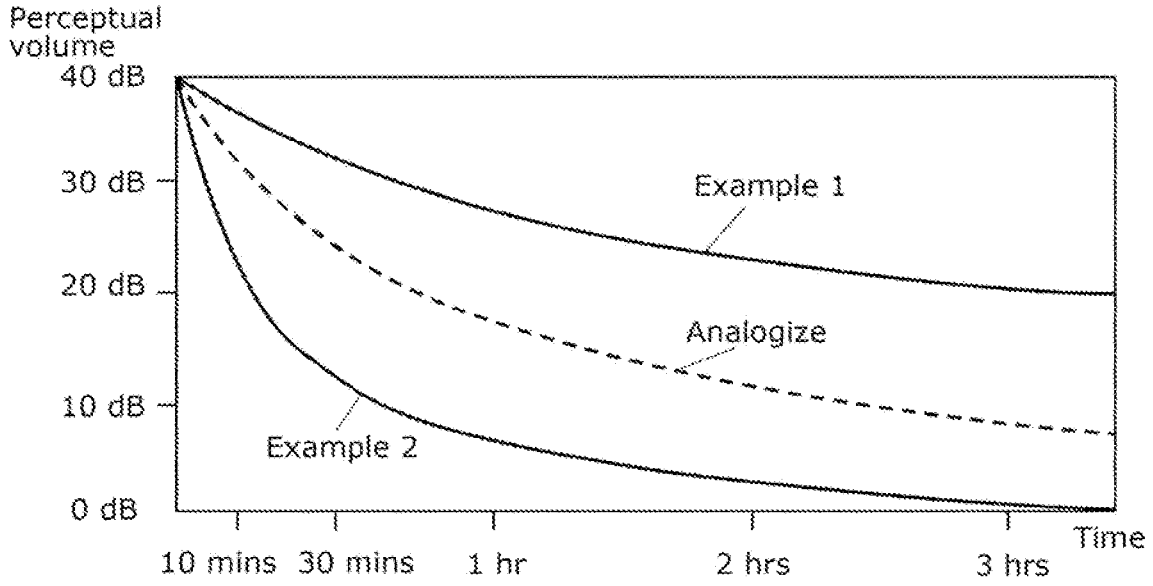
FIG. 10B is a diagram illustrating two examples of the progress of the tinnitus volume during tinnitus treatment sound presentation, which is a diagram for describing analogizing of one example of a TL decrease curve.

FIG. 10B illustrates the TL decrease curves of Example 1 and Example 2.

Although rough approximation could be achieved with a mathematical expression in the example that used scaling for analogizing an RI effect curve that is described above, it was not easy to find a mathematical expression that comprehensively explained both Example 1 (sound source of 50 dB) and Example 2 (sound source of 70 dB). However, the graphs of these two examples do not intersect, and it is possible to analogize a case of a similar example (for example, 60 dB) on a graph as illustrated in FIG. 10B. By referring to even more examples, it was possible to make an analogy with respect to other examples also, including a case of nonlinear scaling.

Further, it is also assumed that, if possible, TL decrease curves will be analogized using a mathematical expression as in the case of scaling in the analogizing of the aforementioned RI effect curve, and not just on a graph.

[Details of Integrated Amount of Sound Stimuli Relating to TL Decrease]

Although there was little change in TL in the case of RI for a short time, it was found that TL changed due to integration of the sound stimuli, and this becomes an effect of long-term masker therapy. Here, in detail, the following has been established.

Integrated amount of sound stimuli (relating to TL decrease)=sound pressure stimulus (relating to TL decrease)+sound change stimulus (relating to TL decrease).

The integrated amount of the sound stimuli, the sound pressure stimulus, and the sound change stimulus are all expressed as an amount of decrease in TL.

The term "sound pressure stimulus" refers to, specifically, the amount of decrease in TL that is due to the sound pressure itself, excluding an element relating to a change in the sound.

In a case where the sound source is a fixed sound (a sound for which the volume, pitch, and waveform [tone] are constant; for example: a musical instrument with little vibrato, or noise with little unevenness), the sound source is considered to have only "sound pressure stimulus".

The "sound change stimulus" is, specifically, an amount of TL decrease that is caused by the stimulus of a sound change. A sound which is accompanied by changes (for example, a "ree, ree" sound made by an insect) or the like changes in volume or pitch or the like in a short time. The change itself affects TL.

Sound sources other than a fixed sound (sounds that change with respect to any of volume, pitch, and waveform) are assumed to have a total of two stimuli, namely, the "sound pressure stimulus" and the "sound change stimulus", and the total thereof is taken as the "integrated amount of sound stimuli".

Here, the integrated amount of sound stimuli, the sound pressure stimulus, and the sound change stimulus are all quantified by how much the TL decreased.

The method for determining each value for a certain sound source, insect sound A, is firstly to simply determine the amount of decrease in TL induced by insect sound A, and the determined value is the "integrated amount of sound stimuli" that insect sound A has as a whole.

Next, in order to take into consideration the sound pressure stimulus as the stimulus amount of only the sound pressure, an averaged sound is synthesized in which all changes (volume, pitch, tone and the like) in insect sound A are eliminated, and the amount of decrease in TL induced by that averaged sound is taken as the "sound pressure stimulus".

Lastly, the sound change stimulus is determined as "sound change stimulus"="integrated amount of sound stimuli"−"sound pressure stimulus".

For example, in a case where the decrease in TL after listening to insect sound A for one hour was 20 dB (integrated amount of sound load), if the decrease in TL after listening to a constant sound with the same average sound pressure as insect sound A for 1 hour was 15 dB (sound pressure stimulus), the sound change stimulus is defined as 20−15=5 dB.

Thus, all the values are quantified by the amount of decrease in TL, and are specifically determined as "sound change stimulus"="integrated amount of sound load"−"sound pressure stimulus".

By this means, the properties of each masker sound source are clarified, and are made use of for analogical inference with respect to other maskers.

The use of these elements is useful for making estimates with regard to other sound sources.

For example, in a case where it is found that the sound change stimulus in a cricket sound source B "ree, ree" has a strong effect, a sound source that further emphasizes the sound change of that sound source is created. The degree of emphasis can be determined by inferring the effect from the data.

For a different sound source, it is possible to estimate the TL decrease curve thereof without directly measuring the sound source, based on another sound source that has a similar sound change stimulus.

In fact, it was found that the sound change stimulus of a certain sound source, insect sound A, produces a strong effect, and an insect sound B in which that change was emphasized was synthesized, and the TL decrease curve for insect sound B was predicted. Data that approximately matched the actual values was obtained, and insect sound B was registered as a useful sound source.

[Details of Integrated Amount of Sound Stimuli in RI Effect]

With respect to the RI effect also, it was found that, similarly to the TL decrease, the amount of sound stimuli can be analyzed as:

Integrated amount of sound stimuli (relating to RI effect) =sound pressure stimulus (relating to RI effect)+sound change stimulus (relating to RI effect).

In this calculation method also, similarly to the above method, for a specific sound source (for example, insect sound A), firstly the RI effect with respect to the insect sound A is taken as the "integrated amount of sound stimuli". Next, a sound source in which changes in the insect sound A have been fixed is created, and the RI effect of that sound source is taken as the "sound pressure stimulus", and the sound change stimulus is then determined as "integrated amount of sound stimuli"−"sound pressure stimulus"="sound change stimulus".

With regard to the RI effect, a sound pressure stimulus caused by a fixed sound, and a sound change stimulus caused by a change have opposite properties to each other. This is because a fixed sound induces a perceptual drift, whilst a change induces a perception update, which inhibits a perceptual drift.

Example

Let us assume that the RI effect immediately after the insect sound A was presented to a patient P for 20 seconds at 50 dB was 15 dB. The tinnitus volume TV during silence of patient P is TL, and in a case where the tinnitus during silence is 40 dB and the tinnitus after sound presentation is 25 dB, 40-25 dB=15 dB is the amount of decrease in tinnitus (the RI effect is 15 dB).

In this case, the integrated amount of sound stimuli=15 dB.

Next, changes in the volume, tone, and pitch (frequency) of the insect sound A are eliminated to generate a sound that is fixed to an average value. Specifically a sound that is fixed at an average frequency distribution is generated. Alternatively, a sound in which changes in the insect sound A have been made as small as possible is generated by a method in accordance with the foregoing method.

Let us assume the RI effect immediately after presenting the sound in a similar manner for 20 seconds at 50 dB to patient P is 20 dB. In this case, the sound pressure stimulus=20 dB.

Therefore, the sound change stimulus can be calculated as sound change stimulus=integrated amount of sound stimuli−sound pressure stimulus=15−20=−5 dB.

Thus, the sound stimuli values that could be analyzed for the insect sound A are:

integrated amount of sound stimuli (15 dB)=sound pressure stimulus (20 dB)+sound change stimulus (−5 dB).

In this regard, as described elsewhere, a fixed sound induces a perceptual drift, whilst a change in sound induces a perceptual update.

A small value of "sound change stimulus" in relation to RI means that there is a negative effect on the RI effect (that is, perceptual drift), and the effect of a change is, conversely, large.

The smaller the sound change stimulus (−5 dB) is in comparison to the sound pressure stimulus (20 dB), the stronger the negative action of the sound change stimulus of the sound source is with respect to RI, which means that the negative action of the sound change stimulus of the insect sound A is strong (the perception updating action is strong).

Here, let us assume that, in addition, a sound in which a change portion of the insect sound A is emphasized is synthesized to generate an insect sound B for which: integrated amount of sound stimuli (5 dB)=sound pressure stimulus (15 dB)+sound change stimulus (−10 dB).

The insect sound B has an even smaller RI effect, which indicates that insect sound B is a sound source which is likely to induce a perception update.

Utilizing this fact, it is possible to select a sound source such as the insect sound B that is less likely to cause perceptual drift at a stage at which the tinnitus recovers from a state in which it was silent for a time.

Further, this recovery curve also can be predicted in more detail by accumulation of data that takes into account the elements of sound pressure stimulus and sound change stimulus.

The measured values were close to predicted values, and efficient control of tinnitus volume was possible.

[Effects of Existing Treatment Techniques and Limitations Thereof]

Here, the effects and the limitations of the existing tinnitus treatment techniques that are considered to have a certain effectiveness are summarized for confirmation.

First, a hearing aid amplifies the sound in a frequency band in which a hearing impairment exists, to thereby generate a sound that should be recognized by the user or a sound that is likely to be familiar to the user. The generated sound is then automatically presented to the user, and thus the hearing aid is ideal as a device for tinnitus treatment. However, it cannot be used by a person who has no hearing loss and is not using a hearing aid.

Further, whilst it has the effect of gradually lowering tinnitus within one day, it is not possible to achieve the objective of immediately reducing tinnitus.

Next, with regard to masker therapy, since the effect of a long-time masker occurs in relation to the frequency distribution of the loaded mask sound, in a case where treatment is performed using an accurate mask sound, an effect of suppressing tinnitus sound is obtained with a relatively high probability.

However, depending on the relationship between the frequency bands of the mask sound and the tinnitus sound, a change can occur in not only the magnitude of the tinnitus sound but also in the pitch or tone thereof. For example, in a case where masking is performed mainly using a lower sound than the tinnitus sound as the mask sound, after the treatment the patient recognizes that a high portion of the original tinnitus sound remains, and the tinnitus sound changed to a higher sound relatively. Therefore, it is necessary to continue the treatment with a mask sound whose pitch and volume are changed to match with the tinnitus sound after the change. However, in the conventional masker therapy, the mask sound cannot be constantly changed so as to cover the frequency band of the tinnitus sound during treatment, and such treatment has not been assumed. Further, the mechanism of tinnitus suppression by masking is unknown, and no further discussion has been made.

In consideration of these effects and the limitations thereof, the inventor of the present application confirmed that by allowing a plurality of patients with a hearing impairment to listen to a sound in a frequency band in which the relevant hearing impairment exists at a volume of a predetermined magnitude or more for a time period of a predetermined length or more in one day using the device according to the present invention that is described below, a state of less tinnitus in comparison to the state before listening to the relevant sound can be continued. In addition, it was confirmed that the tinnitus sound can be efficiently controlled in a more planned manner by utilizing the characteristics of the RI effect curve and the TL decrease curve.

The inventor of the present application considers that if daily tinnitus can be controlled by appropriately presenting a sound load to a tinnitus patient, the tinnitus is favorably under control in a manner comparable to the hearing of an individual with normal hearing.

The device according to the present invention is a device that makes it possible to promote the prevention of the occurrence of errors, or promote the correction of errors, in sound perception in the brain by presenting the patient with a sound load in a frequency band that is missing or lacking, in an appropriate amount and by an appropriate method.

Embodiment

Hereunder, an embodiment of the present invention will be described in detail using the accompanying drawings. Note that, the embodiment described below shows one specific example of the present invention. Thus, the numerical values, shapes, materials, constituent elements, the positions, arrangements and connection forms of constituent elements, respective steps, order of steps, and the like shown in the following embodiment are examples, and are not intended to limit the present invention.

Further, among the constituent elements in the following embodiment, constituent elements that are not described in the independent claims showing the highest concept of the present invention are described as optional constituent elements.

[Configuration]

Figure 12:
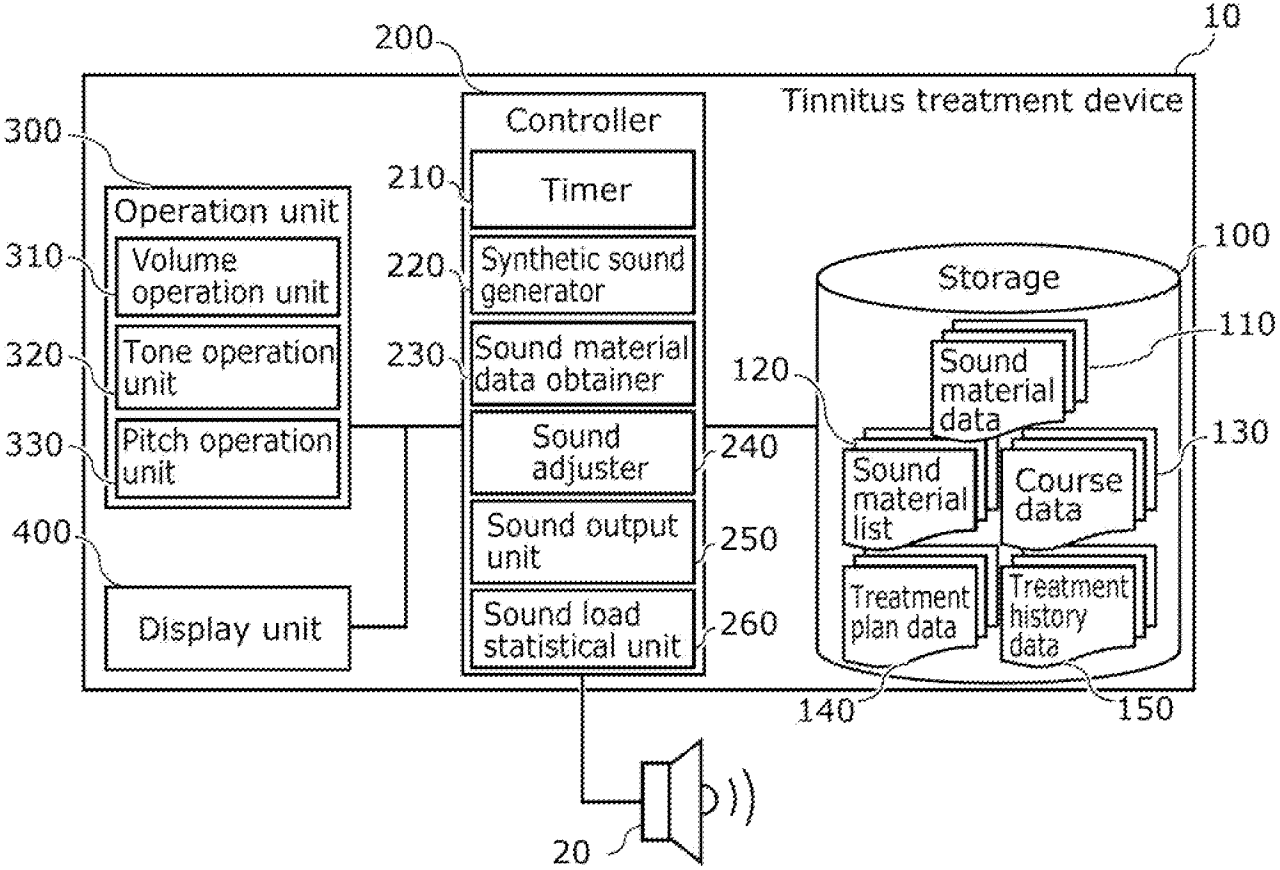
FIG. 12 is a block diagram illustrating the functional configuration of a tinnitus treatment device according to an embodiment.

FIG. 12 is a block diagram for describing the functional configuration of a tinnitus treatment device according to an embodiment of the present invention.

Tinnitus treatment device 10 according to the embodiment of the present invention includes storage 100, controller 200, operation unit 300, and display unit 400.

Note that, in the following description, it is assumed that a user of tinnitus treatment device 10 is, for example, a patient complaining of tinnitus symptoms who listens to a sound using tinnitus treatment device 10, or a health care professional such as a doctor or a family member who causes the patient in question to listen to a sound using tinnitus treatment device 10.

Storage 100 stores data that is used by tinnitus treatment device 10. Such data includes sound material data 110, sound material list 120, course data 130, treatment plan data 140, and treatment history data 150. The details of the aforementioned data are described later using examples. Further, a program (not illustrated in the drawing) which controller 200, described later, reads and executes is also stored in storage 100. It is possible to realize this kind of storage 100 by using, for example, a semiconductor memory such as a flash memory. Storage 100 may also be realized by a combination of various kinds of memory devices such as a HDD (Hard Disk Drive), a ROM (Read-Only Memory), and a RAM (Random Access Memory). Further, all or one part of storage 100 may be removable from tinnitus treatment device 10 so as to be replaceable. By this means, for example, by replacing an SD card including a flash memory storing the aforementioned data other than the program, one tinnitus treatment device 10 can be utilized by a plurality of patients.

Controller 200 is realized using, for example, a microcontroller, and reads and executes the program stored in storage 100 so that tinnitus treatment device 10 exhibits a predetermined function. In accordance with the program or, in addition, in response to an input from operation unit 300 which is described later, controller 200 performs acquisition and processing of the each of the data items described above, output of data obtained by the processing, and control of other constituent elements. Note that, in a case where controller 200 is realized using a microcontroller, it should be understood that a memory device that is one part thereof is included in storage 100 of tinnitus treatment device 10 in a functional sense.

Timer 210, synthetic sound generator 220, sound material data obtainer 230, sound adjuster 240, sound output unit 250, and sound load statistical unit 260 are included in controller 200.

Timer 210 is, for example, a clock such as an RTC (real-time clock), and performs timekeeping for processing relating to time in respective processing operations, described later, performed by controller 200.

Synthetic sound generator 220, sound material data obtainer 230, sound adjuster 240, sound output unit 250, and sound load statistical unit 260 are functional constituent elements provided by controller 200 that reads and executes the program from storage 100.

Synthetic sound generator 220 generates temporary sound material data by calculating waveform data based on a mathematical expression for synthesizing a sound, that is, a sound waveform, for example, a mathematical expression for calculating a sine wave or band noise, and sends the generated sound material data to the sound material data obtainer. The mathematical expression is stored in storage 100 as a part of the program or as data (not illustrated) that is referred to by the program. The sound material data which synthetic sound generator 220 generates is determined, for example, in accordance with an operation for selecting sound settings such as the tone or pitch which a user performs through operation unit 300 which is described later, or by referring to course data 130 to determine the sound material data to be generated based on course settings included in course data 130.

Sound material data obtainer 230 obtains temporary sound material data generated by synthetic sound generator 220 or sound material data 110 indicating a plurality of sounds that are different from each other which is stored in storage 100. Sound material data 110 that sound material data obtainer 230 obtains is determined, for example, in accordance with an operation for selecting sound settings such as the tone or pitch which a user performs through operation unit 300 which is described later, or by referring to course data 130 to determine the sound material data to be obtained based on course settings included in course data 130.

The aforementioned sound material data is, for example, a plurality of audio data files indicating sounds that are different from each other. The course data is data that shows a schedule (hereinafter also referred to as "course settings") relating to treatment sounds that a plurality of audio data files indicate. The course data is prepared in advance or is created by a user and saved in storage 100. FIG. 13A is a diagram illustrating an example of the data structure of course data 130.

Figure 13B:
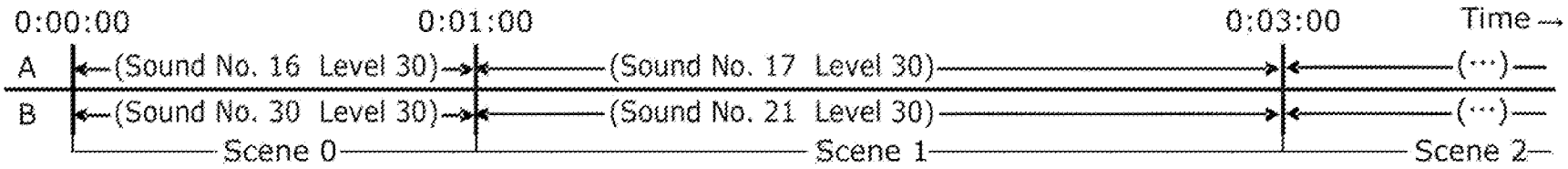
FIG. 13B is a diagram illustrating the content of one course included in the aforementioned example of course data in time series.

In this example, course data 130 is in table format, and in each data row, a scene is shown that includes a combination of two sounds to be reproduced in parallel (sound no.—A, sound no.—B), a time length for which the combination is reproduced (time hh:mm:ss), and a reproduction level of each sound (reproduction level—A, reproduction level—B), in other words, the volume setting. Further, a course is a collection of a plurality of scenes, for which the order in which to perform the scenes has been determined. In this example of course data 130, a number indicating a course and a number indicating a scene belonging to the course are input in the leftmost column, with the scene number also indicating the order. Course 01 includes 16 scenes from scene 00 to scene 15 in that order. FIG. 13B illustrates, in time series, the order of reproducing sounds for about 3 minutes from the beginning of course 01 in this example of course data 130.

The effect of reproducing two sounds in parallel is described later.

Note that, although the phrase "reproducing two sounds in parallel" corresponds to mixing two sounds and outputting the sounds as a mono sound in the case of the aforementioned device which the inventor manufactured by way of trial, the meaning of the phrase is not limited thereto. The phrase refers to superimposing and reproducing sounds, regardless of whether a sound that is output is mono sound or stereo sound.

Each course included in course data 130 is displayed through display unit 400, described later, so as to be selectable by a user.

For example, in a case where the user operates operation unit 300 and selects course 01, sound material data obtainer 230 that received a command indicating this selection obtains sound material data in accordance with the sound numbers to be reproduced in the respective scenes included in course 01.

Note that, sounds in the categories mentioned hereunder are included in the sounds that are reproduced, in consideration of the effect of suppressing or alleviating tinnitus and the ease of continuing therapy using tinnitus treatment device 10.

(1) Noise (Wide-Range Frequency Band)

Various kinds of colored noise such as white noise and pink noise are included in this category. Since such noise includes sound in a wide range of frequencies, many tinnitus sounds are targets for masking with such noise, and although it is difficult to obtain a masking effect of a high level in comparison with the sounds of categories (2) and (3) described below, selection of the frequency need not be strict. Further, such noise is expected to have an effect of obscuring the tinnitus and providing comfort to the user.

(2) Noise (Narrow-Range Frequency Band)

Examples of sounds included in this category include band noise that is centered on a predetermined frequency and that is over a narrow frequency band compared to the noise described above. Although it is necessary to adjust the pitch of such noise to the pitch of the tinnitus somewhat exactly in comparison to a wide-range frequency band, such noise is expected to exert an effect of effectively masking tinnitus with a low volume.

Note that, sound in this category that is used as a treatment sound is not limited to band noise that conforms to official standards. The inventor has confirmed that as long as noise has a peak at a specific frequency in the frequency distribution in question, the noise can exert a similar effect.

The term "band noise" as used herein is an expression used as a representative example of sounds included in the present category, and the term can be read as meaning noise generally that has a peak at a specific frequency in the frequency distribution and applied as a treatment sound.

(3) Tones (Scaled Musical Instrument Sounds)

The so-called "do-re-mi" scale sounds of scaled musical instruments such as violins and organs are included in this category. It is expected that such a sound will mask tinnitus extremely effectively by allowing the user to listen to a sound whose pitch has been exactly matched to the pitch of the tinnitus.

(4) Tones (Synthetic Sounds)

Whilst these are scale sounds similarly to (3), these are extremely monotonous sounds obtained by eliminating sound changes such as vibrato and reducing harmonic overtones. Such sounds are obtained by synthesizing, for example, by an electronic technique. A more specific example is a sound that a synthesizer that is a so-called electronic musical instrument can output.

Because there are few harmonic overtones included in such sounds, in order to obtain a tinnitus masking effect it is necessary to match the pitch to the tinnitus even more exactly than the sounds described in (3). However, unlike the sounds of any of the other categories that tinnitus treatment device 10 outputs, because a sound without temporal changes can be created, there is a possibility that the sound can have a special effect in tinnitus treatment.

(5) Environmental sounds

Sounds that are present in the natural environment and towns and the like are included in this category. Rain sounds, water sounds of rivers and beaches, chirping of birds or insects, and the sound of crowds may be mentioned as specific examples of such sounds. It is expected that by providing such sounds as a sound load, for example, an effect that obscures tinnitus and provides comfort will be exerted.

Note that, each sound belonging to at least the aforementioned categories (1) to (4) is a stationary sound with respect to which there is almost no level fluctuation within the time period for which the sound is reproduced or for which the level fluctuation is negligibly small, or is a sound that is close to a stationary sound.

Information relating to these categories and the sounds that belong to each category may also be presented to the user who sets the scenes and creates the course. For example, sound material list 120 illustrated in FIG. 14 is a list that very simply includes such information. If such a list is stored in storage 100, the list may be acquired by controller 200 and presented to the user on display unit 400, or may be referred to in order to obtain sound material data.

Note that, although there is an entry "silence" for sound no. 0 in sound material list 120 shown in FIG. 14, this entry is included so that settings can easily be made to create a section in which one sound is reproduced at a time or in which there is silence, and there is no audio file of silence that corresponds to this entry. However, means for realizing a section in which one sound is reproduced or in which there is silence is not limited thereto.

Further, sound material data which synthetic sound generator 220 generates in accordance with an operation for selecting a tone or a pitch that the user performs through operation unit 300, to be described later, may also be registered in sound material list 120 to facilitate creation of a course. In the example in FIG. 14, the sound material data of such a synthetic sound is registered in sound nos. 61 and 62. In this case, a parameter that determines the frequency characteristic of each synthetic sound that is registered is also stored in storage 100, and synthetic sound generator 220 generates sound material data of a registered synthetic sound as the need arises by using the parameter and a mathematical expression for synthesizing the sound waveform as necessary.

Note that, among the categories described above, with respect to the sounds of categories (1) to (4), since temporary sound material data that synthetic sound generator 220 generates is used, sounds can be output which have a higher effect on suppressing or alleviating the tinnitus of the patient who is the user compared to existing sounds. Further, because the sounds in these categories are stationary sounds or sounds that are close to a stationary sound, power consumption for generating the data is low as described above. Therefore, even in a case where tinnitus treatment device 10 is a compact size that is easy to carry and operates with a power supply from a battery having a limited capacity, it is possible to continuously use tinnitus treatment device 10 for a time length which is desirable for acoustic therapy of tinnitus.

Furthermore, sound material data which the user prepared according to their preference or the like, for example, sound material data obtained by recording a performance of a specific musical composition or environmental sound, may be stored in storage 100, and may also be registered in sound material list 120. In the example illustrated in FIG. 14, the sound material data of such a sound is registered as sound no. 63.

In tinnitus treatment device 10, sound signals indicating two sounds which are different to each other which were selected by the user from among these sounds and which are sounds to be reproduced in parallel as treatment sound are output using sound material data stored in the storage or sound material data that synthetic sound generator 220 generates, or using both of these.

Sound adjuster 240 changes the sound material data obtained by sound material data obtainer 230, or adjusts the output level of the sound indicated by the sound material data. Sound adjuster 240 performs such an operation, for example, by referring to course data 130 and performing the operation based on course settings which course data 130 indicates, or in accordance with an operation that the user performs through operation unit 300, described later, to select the tone or pitch or to change the sound settings such as the volume or the volume balance between two sounds.

For example, sound adjuster 240 controls an amplification circuit (not illustrated in the drawings) which tinnitus treatment device 10 further includes, so that the sound is output at a volume according to the setting of the reproduction level of each sound included in the scene.

Further, in a case where the user performs an operation on operation unit 300 to change the reproduction level (absolute volume) of the treatment sound overall or of each sound, or to change the balance (volume ratio) of the reproduction levels of the two sounds, upon receiving the command indicating the content of the operation, sound adjuster 240 controls the aforementioned amplification circuit so that the sound is output at the reproduction level according to the received command.

Furthermore, in a case where the user performs an operation on operation unit 300 to select and reproduce any sound, upon receiving the command indicating the content of the operation, sound adjuster 240 causes sound material data obtainer 230 to obtain the sound material data of the relevant sound. Alternatively, if the operation performed by the user is an operation for changing to a sound which is to be reproduced using sound material data to be generated by synthetic sound generator 220, sound adjuster 240 causes synthetic sound generator 220 to generate sound material data indicating the sound after the change.

Sound adjuster 240 may accept such a user operation at any time and operate as described above even when tinnitus treatment device 10 is reproducing two sounds in parallel as a treatment sound. For example, in a case where the user performs an operation on operation unit 300 to change either one of the two sounds that are being reproduced to another sound, sound adjuster 240 may cause sound material data obtainer 230 to obtain sound material data indicating the other sound, and after adjusting the reproduction level as necessary, may then cause sound output unit 250 to output the sound signal.

By this means, for example, in a case where the magnitude, pitch, sound quality or the like of the tinnitus sound of the patient changes during use of tinnitus treatment device 10, and the sound from tinnitus treatment device 10 at that time does not adequately mask the tinnitus sound or feels uncomfortable for the patient, the patient themselves can quickly change the sound to an appropriate sound. Accordingly, the effect of treatment by tinnitus treatment device 10 is enhanced. Moreover, enhancement of the effect of treatment, the reduction in discomfort, and the sense of security obtained from the fact that the user can control tinnitus treatment device 10 themselves encourages the user to continue treatment using tinnitus treatment device 10.

Sound output unit 250 outputs a sound signal indicating the sound after the sound was adjusted by sound adjuster 240. In the example illustrated in FIG. 12, this sound signal is output to loudspeaker 20 which is outside tinnitus treatment device 10. Loudspeaker 20 is, for example, a loudspeaker of an earphone or a headphone that is connected by wire or wirelessly so as to receive an input of a sound signal from tinnitus treatment device 10. Upon receiving the input of the sound signal from tinnitus treatment device 10, loudspeaker 20 generates a sound according to the sound signal. Loudspeaker 20 is an example of a sound presentation unit in this example.

The patient listens to the sound generated in this way as a treatment sound for tinnitus treatment. As mentioned above, this treatment sound is a sound obtained by reproducing two sounds in parallel, and sound settings such as the volume of each of these sounds or of the overall treatment sound, the volume ratio between the two sounds, the selected sounds and the combination thereof which are sound settings that are effective for treatment are automatically proposed using the RI effect curve, the TL decrease curve, and the like.

Among these, the doctor may recommend sound settings from a medical point of view, or the patient themselves may select and decide sound settings according to the tinnitus sound which the patient themselves perceives. Further, the sound settings may be changed by an operation performed by the patient according to a change in the tinnitus sound during use or the psychological circumstances.

Sound load statistical unit 260 collects statistics relating to a sound load provided by causing the patient to listen to a treatment sound in this manner, and includes results pertaining to the collected statistics in treatment history data 150 and stores the data in storage 100. FIG. 15 is a diagram illustrating an example of the data structure of treatment history data 150.

In this example, the following items are recorded in relation to output of a sound load which controller 200 actually performed: the date (YYYYMMDD represents the year in 4 digits, the month in 2 digits, and the day in 2 digits), and the reproduction order (Nos.) and combination (A/B were reproduced in parallel) for that date; the time length (hh:mm:ss represents two digits for each of hours, minutes, and seconds); the kind of sound (sound material data No.) that was output and the frequency (or frequency band) thereof; the reproduction level; and the load score. The term "load score" refers to the product of volume and time (in this example, in minute units), and is an example of a statistic relating to the sound load in the present embodiment.

Note that, a statistic relating to the sound load is not limited to this example, and for example, only the time length may be used. Further, a statistical value that is additionally obtained from the data in the example illustrated here, for example, a daily sum of the product of volume and time length which is calculated for each predetermined frequency band may be used. The items of treatment history data 150 are also not limited to the items described in FIG. 15, and items may be further added or some items may be deleted. For example, the item for the calculation result of the load score may be omitted, and the load score may be calculated as necessary by other processing. Further, the method of calculating the load score is not limited to the above example.

Sound load statistical unit 260 further compares treatment history data 150 with treatment plan data 140 stored in storage 100, and presents the result of the comparison to the user via display unit 400.

The term "treatment plan data 140" refers to data showing a treatment plan created based on the results of an examination performed on the patient by a doctor or the like. FIG. 16 illustrates an example of the data structure of treatment plan data 140. In the example illustrated in FIG. 16, a plan no., frequency band, and load score are included as items of treatment plan data 140.

The term "treatment plan" mentioned here refers to a plan relating to the amount of sound a patient should be caused to listen to in a predetermined period, for example, each day, in other words, the size of a load for each frequency band of a sound load that should be presented for the purpose of suppressing tinnitus. A treatment plan indicating such a sound load is, for example, decided by a doctor based on characteristics of the tinnitus that are expressed by pitch-match and volume which are the results of an examination performed on the patient, or based on a program which is based on an RI effect curve or a TL decrease curve obtained from a frequency band of a hearing impairment identified by [a tinnitus] *an audibility* examination. Furthermore, before the start of the treatment or after the start of the treatment, appropriate changes may be made that take into consideration the subjectivity of the patient.

Further, the term "comparison" refers to, in this example, the load score. The result of a comparison that is presented may be a difference between load scores, or may be a ratio of the load score of treatment history data 150 with respect to the load score of treatment plan data 140.

By showing the patient the result of a comparison between treatment plan data 140 showing such a treatment plan and treatment history data 150 showing the actual result of the treatment which the patient underwent, self-management of the treatment becomes easier for the patient. For example, it is not necessary for the patient to count the number of times that a course should be repeated in one day, and the patient can easily know what percentage of the course has been completed in a case where the treatment was interrupted during use, and it is thus easy for the patient to use tinnitus treatment device 10 even in a case where the patient cannot take a large block of time for each treatment session.

Operation unit 300 is a constituent element that is operated by the user to perform course settings, or to change the volume, the kind of sound (tone), or the pitch during use of tinnitus treatment device 10, and is realized by keys, buttons, sliders, dials or the like which are physical components or which are displayed as images of display unit 400 by means of software. Operation unit 300 includes volume operation unit 310, tone operation unit 320, and pitch operation unit 330, which are used for changing the volume, tone, and pitch, respectively.

Display unit 400 displays a screen showing the operational status of tinnitus treatment device 10, a setting screen, a screen showing a comparison result obtained by sound load statistical unit 260, and the like, and is realized, for example, by a display device using liquid crystal or organic electro-luminescence or the like. Alternatively, lighting equipment such as a pilot lamp may also be used.

Figure 17A:
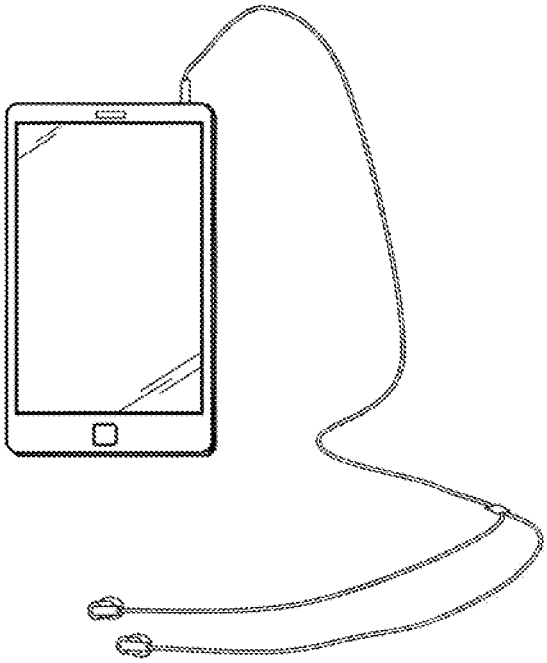
FIG. 17A is a diagram illustrating an example of the tinnitus treatment device according to the embodiment.

Such kind of tinnitus treatment device 10 can be realized, for example, by using a portable information terminal as illustrated in FIG. 17A. In this case, storage 100 is realized by a memory device of the portable information terminal, and operation unit 300 and display unit 400 are realized by a touch panel of the portable information terminal. Operation unit 300 may also be realized by using physical buttons or the like of the portable information terminal.

Controller 200 is realized by an arithmetic processing unit of the portable information terminal executing a program for providing each functional constituent element, which is stored in storage 100. Loudspeaker 20 is a sounding body such as an earphone that is connected to the portable information terminal.

Figure 17B:
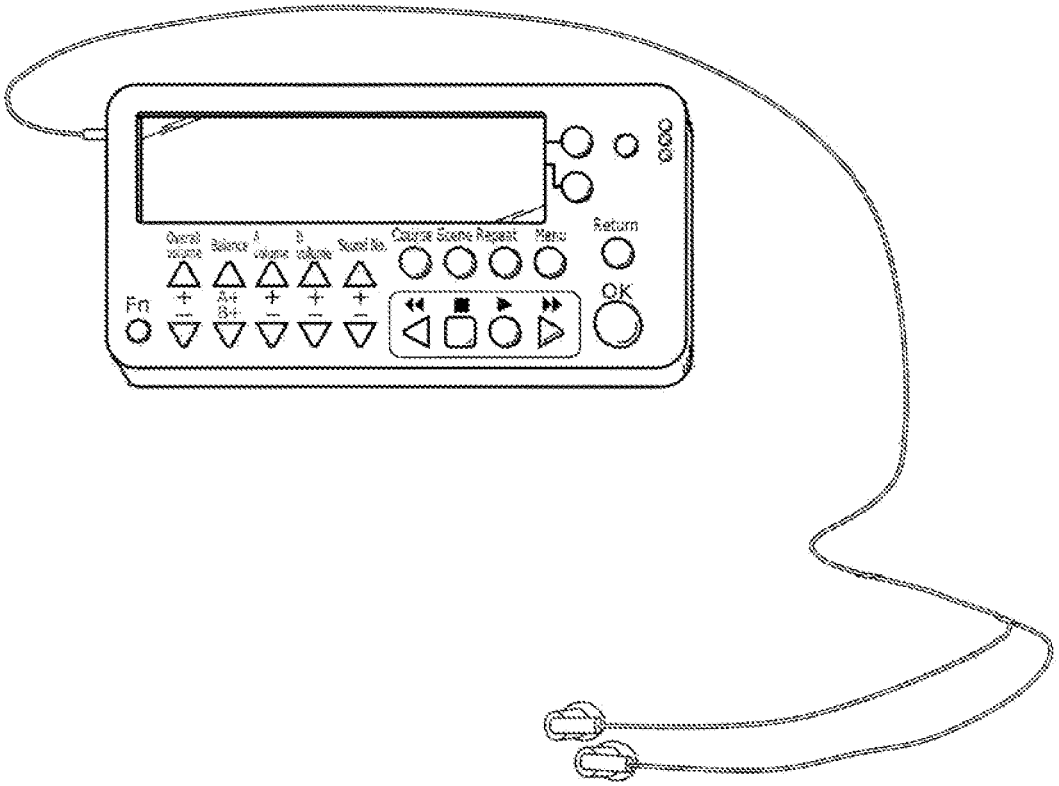
FIG. 17B is a diagram illustrating an example of the tinnitus treatment device according to the embodiment.

Further, tinnitus treatment device 10 may be realized, for example, using a dedicated device which is illustrated as an example in FIG. 17B. In this case, storage 100 is realized by a memory device which the dedicated device includes. Operation unit 300 is realized by buttons of the device. In the illustrated example, volume operation unit 310 is realized by buttons for the overall volume, balance, A volume, and B volume which are provided on the device main body. Further, tone operation unit 320 and pitch operation unit 330 are realized by buttons for sound numbers that are used for making a selection from the sound material list illustrated in FIG. 14. Display unit 400 is realized by a display device on the upper left side of the main body of the device. Controller 200 is realized by the microcontroller of the device executing a program for providing each functional constituent element, which is stored in storage 100. Loudspeaker 20 is a sounding body such as an earphone that is connected to the device.

Whilst the configuration of tinnitus treatment device 10 has been described thus far, the constituent elements of tinnitus treatment device 10 also include constituent elements other than the constituent elements described able. For example, respective tinnitus treatment devices 10 illustrated in FIG. 17A and FIG. 17B have portability so that it is possible to use tinnitus treatment device 10 at a location away from the home or office or the like, and it need hardly be said that to enable such use tinnitus treatment device 10 includes a power source including a function for charging a chargeable battery that supplies operating power to each constituent element of tinnitus treatment device 10

Furthermore, tinnitus treatment device 10 is not limited to a device which has portability as illustrated in FIG. 17A and FIG. 17B. For example, tinnitus treatment device 10 may be realized by the respective functional constituent elements of controller 200 being provided and the respective data items to be stored in storage 100 being stored and managed in a memory device by using a processor of a personal computer to execute a program installed in the personal computer. In addition, tinnitus treatment device 10 may be realized as a dedicated device for a medical facility or for domestic use.

Further, tinnitus treatment device 10 which has portability and tinnitus treatment device 10 which does not have portability may be used in combination for daily treatment, and various kinds of settings, treatment plan data, and treatment history data 150 may be communicated and synchronized between both tinnitus treatment devices 10.

[Operation]

The operation of tinnitus treatment device 10 will be described in accordance with a usage example using the device illustrated in FIG. 17B as an example.

Figure 18A:
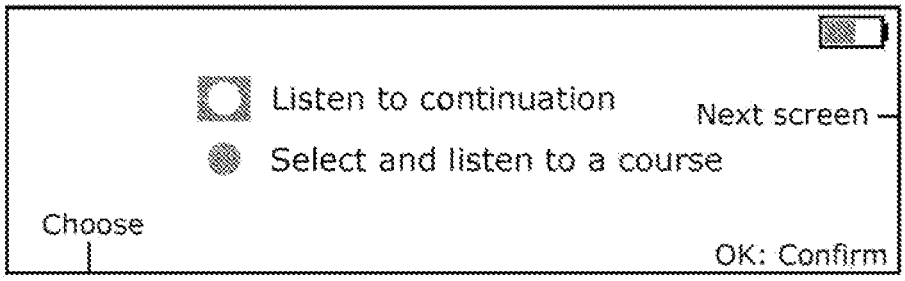
FIG. 18A is a diagram illustrating an example of a screen displayed on the tinnitus treatment device according to the embodiment.
Figure 18B:
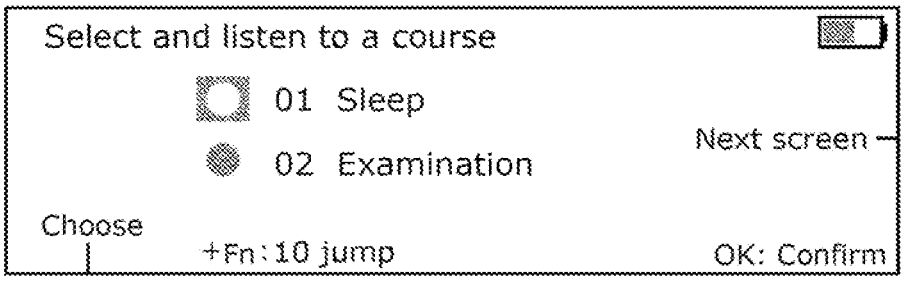
FIG. 18B is a diagram illustrating an example of a screen displayed on the tinnitus treatment device according to the embodiment.

FIG. 18A to FIG. 18H are views illustrating examples of screens that are displayed on tinnitus treatment device 10 illustrated as an example in FIG. 18B.

FIG. 18A is an example of a screen that is displayed when tinnitus treatment device 10 is started. On this screen, the user selects an item using a button "Overall Volume" and presses an OK button to confirm the selection.

FIG. 18B is an example of a screen that is displayed in a case where "Listen To A Course" is selected on the screen shown in FIG. 18A. On this screen, the user selects a desired course from among the courses stored in tinnitus treatment device 10, and presses the OK button to confirm the selection.

Figure 18C:
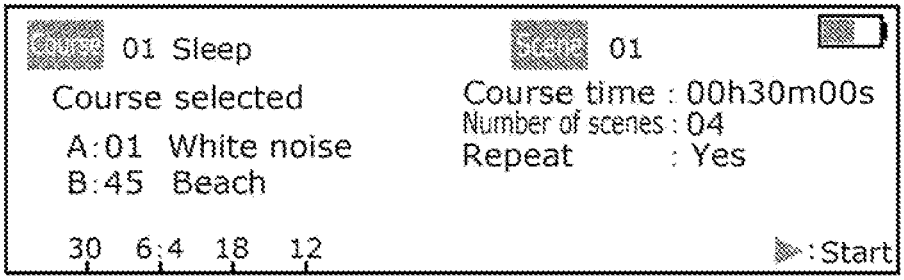
FIG. 18C is a diagram illustrating an example of a screen displayed on the tinnitus treatment device according to the embodiment.

FIG. 18C is an example of a screen that is displayed when the user selected a course on the screen illustrated in FIG. 18B. On this screen, the user can check information relating to the selected course. In this example, information such as the name of the course, the total time of the course, the number of scenes included in the course, the sound that is output in the initial scene, and the volume of the sound is displayed.

If the course selection is appropriate, the user can press a "Play" button to start to listen to the sound.

The volume is shown by numerical values at the bottom left of the screen, and in this example, in order from the left side, "30" that is the volume of the treatment sound as a whole, "6:4" that is the balance (volume ratio) between the two sounds, "18" that is the absolute volume of A, and "12" that is the absolute volume of B are shown. These settings can be selected from numerical values that change each time a corresponding button that is below the screen is pressed.

Figure 18D:
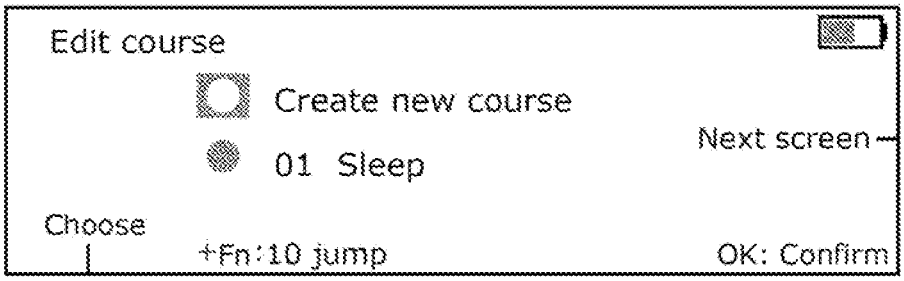
FIG. 18D is a diagram illustrating an example of a screen displayed on the tinnitus treatment device according to the embodiment.

FIG. 18D is an example of a screen displayed in a case where, on the screen illustrated in FIG. 18A, the next screen is displayed (by downward scrolling) and course editing is selected. On this screen, the user newly creates a course or selects an existing course to edit.

Figure 18E:
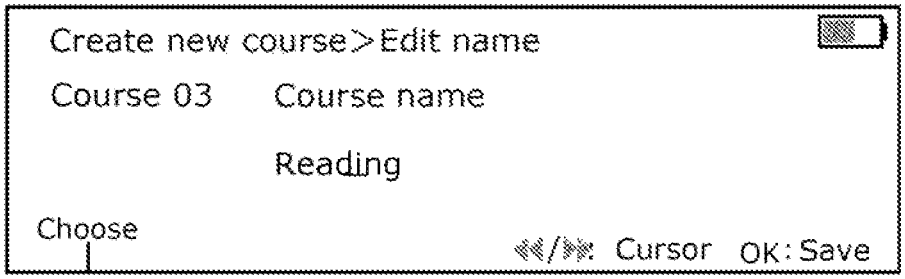
FIG. 18E is a diagram illustrating an example of a screen displayed on the tinnitus treatment device according to the embodiment.

FIG. 18E is an example of a screen displayed in a case where the user selected to newly create a course on the screen illustrated in FIG. 18D. On this screen, users input a name for the course using buttons.

Figure 18F:
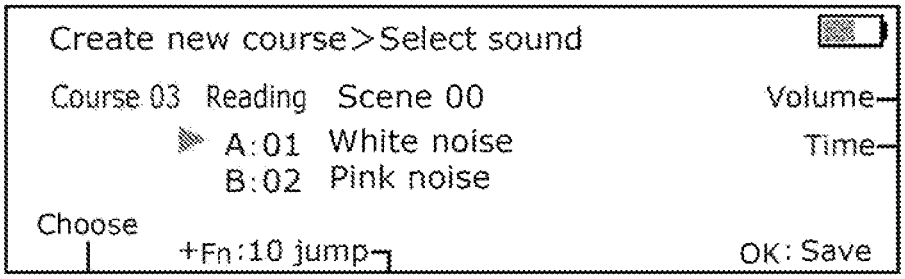
FIG. 18F is a diagram illustrating an example of a screen displayed on the tinnitus treatment device according to the embodiment.

FIG. 18F is an example of a screen for setting a scene to be included in the course for which a name was input on the screen illustrated in FIG. 18E. In this example, two sounds to be reproduced in parallel are selected for scene 00 that is the initial scene of a course that was named "Reading". By pressing the OK button in a state in which the name of a desired sound is displayed, the user can include a sound to be reproduced in this scene in the course data shown in FIG. 15 and save this setting in storage 100.

Figure 18G:
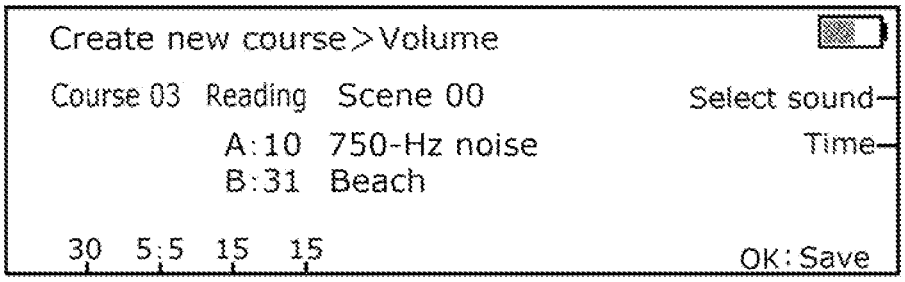
FIG. 18G is a diagram illustrating an example of a screen displayed on the tinnitus treatment device according to the embodiment.

FIG. 18G is an example of a screen for setting the volume of the sounds to be reproduced in scene 00. In this example, the four numerical values at the bottom left of the screen can be selected from numerical values that change each time a corresponding button below the screen is pressed. These numerical values indicate, in order from the left side, the volume of the treatment sound as a whole, the balance (volume ratio) between the two sounds, the absolute volume of sound A, and the absolute volume of sound B. By pressing the OK button in a state in which a numerical value that indicates the desired volume setting is displayed, the user can include the volume of a sound to be reproduced in this scene in the course data shown in FIG. 15, and save this setting in storage 100.

Figure 18H:
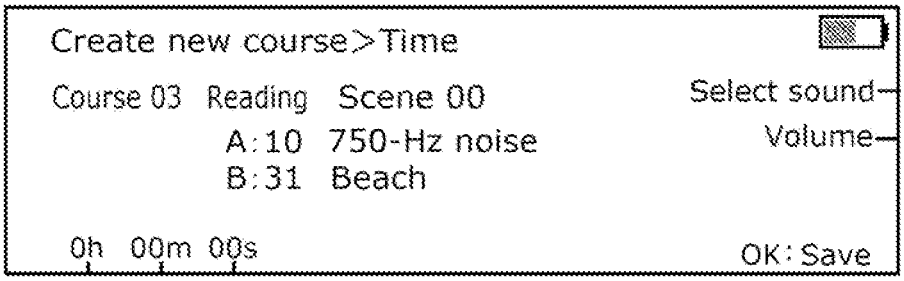
FIG. 18H is a diagram illustrating an example of a screen displayed on the tinnitus treatment device according to the embodiment.

FIG. 18H is an example of a screen for setting the time length of scene 00. In this example, the three numerical values at the bottom left of the screen can be selected from numerical values that change each time a corresponding button below the screen is pressed. These numerical values indicate, in order from the left side, hours, minutes, and seconds. By pressing the OK button in a state in which a numerical value indicating the desired time length of this scene is displayed, the user can include the time length for this scene in the course data shown in FIG. 15, and save this setting in storage 100.

By performing similar operations, the sounds to be reproduced, the volumes of the sounds, and the time length of the scene are set for the scenes following scene 00. When selection of the settings for each scene included in the course in question as well as the order of these scenes have been input through operation unit 300 and saved in storage 100, creation of the course is completed, that is, a schedule relating to a plurality of treatment sounds is determined.

Note that, the screens that are displayed on tinnitus treatment device 10, the mode of operating operation unit 300, and the contents of possible settings are not limited to the above examples. For example, a screen for creating a sound that is set by the user may be transitioned to from the screen for selecting a sound. Further, the order between a plurality of scenes for which selection of settings has been generally completed once may be interchangeable. Alternatively, settings of a plurality of scenes including at least the selection of sounds may be stored in storage 100 regardless of a course, and thereafter a course may be created by the user selecting the order of scenes which are selected from among these stored scenes and also selecting settings (volume and time length) that are necessary to supplement the settings for each scene.

Also, whilst selection of the sound and the volume is also included in the settings of the scene as described above, these setting may also be changeable at any time using operation unit 300 during reproduction. Further, it may also be possible to overwrite and save a sound or a volume which was changed during reproduction, as the setting for the sound or volume of the relevant scene. In addition, in a case where the volume setting is changed in one scene included in a certain course, the volume setting of other scenes included in the relevant course may also be automatically changed. By this means, the time and trouble required for the user to adjust the volume each time the scene changes during execution of a certain schedule is reduced. Further, this kind of automatic change of the setting is not limited to the volume, and may also be executed with respect to the kind or pitch of the sound. This kind of function of tinnitus treatment device 10 for reducing the time and trouble of the user is described later in the next section.

Tinnitus treatment device 10 which can be used in this way is easy to use by being incorporated into daily life, even for a tinnitus patient who does not need to use a hearing aid. Further, since there are various combinations of sound load settings, tinnitus treatment device 10 can be used for respective patients with different tinnitus symptoms, and is also adaptable to changes in the tinnitus symptoms of a single patient. In addition, since it is possible to provide a sound load according to the situation of use or the patient's own preference or a sudden request, improvement in the frequency of use by the patient as well as continuation of use can be promoted.

[Setting of Sound Load]

[Policy for Setting Sound Load]

The sound load provided to the patient by causing the patient to listen to a treatment sound of a certain magnitude for a certain time period using tinnitus treatment device 10 can be flexibly set with regard to the (kinds of) sounds and the combination of sounds, and also the volume and balance and the like as described above. However, in order to obtain an effect, it is necessary that an appropriate sound load is provided in an appropriate amount.

A treatment sound that is used for an appropriate sound load here is a sound with a volume, tone, and pitch in accordance with the frequency band in which the hearing ability of the patient is impaired and the perceived tinnitus of the patient.

On the other hand, in order to provide an appropriate amount, it is desirable that voluntary continuation of use by the patient is encouraged, and at least subjecting the patient to any discomfort by provision of a sound load should be avoided. From this viewpoint, one task is to avoid excessive monotones and to use a sound load that is as comfortable as possible for the patient.

Furthermore, the purpose of providing variation in the treatment sounds is not simply to avoid monotony. As described above, depending on the relationship between the frequency bands of the mask sound and the tinnitus sound, after masking is performed, a change can occur not only in the magnitude of the tinnitus sound, but also in the pitch or tone. Masker therapy obtains an effect that masks tinnitus by covering the frequency band of the tinnitus and causing the patient to listen to a sound with a higher volume than the tinnitus.

However, when using tinnitus treatment device 10, masking tinnitus is only one of the indicators for setting the treatment sound, and the hearing impairment band in general is targeted, and the volume need not necessarily be of a magnitude that masks the tinnitus. For example, the volume may be of a magnitude such that the tinnitus no longer bothers the patient. Therefore, in a strict sense, a treatment sound which a patient is caused to listen to with tinnitus treatment device 10 differs from the conventional masker therapy. Further, the main point is to integrate the time and to apply a sufficient sound load in the target band.

Tinnitus has a specific frequency in the impaired frequency region of the patient, but does not include all of the frequencies. Although it is unclear what determines the frequency of tinnitus among the impaired frequency region, it is considered that the tinnitus frequency is determined by the course of the pathology of the patient, the sound environment, and the like. A change in the tinnitus sound after masking is performed is also one example where the frequency of tinnitus is determined by the sound environment.

In order to correspond to tinnitus sound that changes in this way, tinnitus treatment device 10 is configured so that the sounds which the patient listens to can be changed. To realize such kind of changes in sounds, a technique whereby the treatment sound is determined in advance in consideration of a change in the sound before applying the sound load, and a technique whereby the patient themselves changes the treatment sound during provision of the sound load are available. These techniques may be used in combination.

[Technique for Determining Treatment Sound]

First, one example of a technique for determining the treatment sound before provision of the sound load will be described. In this technique, the following two points are considered together.

(1) Characteristic of tinnitus expressed by at least one of pitch match and volume as a result of a tinnitus examination; and (2) Hearing impairment band identified by [a tinnitus] *an audibility* examination.

Here, (1) is treated strictly as a symbolic characteristic. Further, (2) is used as a range in which it is assumed that tinnitus can occur. Note that, tinnitus fluctuates within the band of (2) depending on the situation. In this regard, first, a sound having a characteristic that is the same as or similar to a characteristic of tinnitus obtained using pitch match and volume is taken as the main body of the treatment sound. Further, on the assumption that the tinnitus deviates from the sound having this characteristic to the periphery thereof, a sound having a sound range that is expanded from this sound is further selected. Two sounds, that is, the sound as the main body and the sound with a wide range which were determined in this manner are changed once or are changed over time in the width of this range and presented as a treatment sound.

[Selection of Treatment Sound Using RI Effect Curve]

An effective treatment sound is selected and a temporal program for the treatment sound is selected by collecting, defining and analogizing data in each patient group from the viewpoint of a perceptual drift due to a sound stimulus being constant and from the viewpoint of a perception update due a sound stimulus changing, when totaling the RI effects of the respective sound sources.

Example

RI effect curve under the same 50 dB load of sound source A for the same patient P1 (extract)

TABLE 5

| Sound source presentation time | 5 secs | 10 secs | 30 secs | 1 min |
|---|---|---|---|---|
| RL (Tinnitus volume immediately after presentation finishes) | 40 dB | 30 dB | 20 dB | 20 dB |

After sound source A was presented at 50 dB for 30 secs, although the recovery time was usually 10 minutes after the tinnitus volume reached 20 dB, by presenting sound source S (20 dB) at one-minute intervals after cessation of sound source A, the tinnitus recovery time was extended to 30 minutes.

Example

Sound source A2 and sound source B2 were assumed for a certain patient P2, based on [a tinnitus] *an audibility* examination, pitch match, and a volume examination with respect to patient P2. An RI effect curve for each frequency in a case where a total of 50 dB of A2 and 40 dB of B2 were presented for 10 secs each to patient P2 was assumed, and the state of a recovery period in the curve was also assumed, and an integrated value of the perceived amount of tinnitus for five minutes was also derived. Since the degree of suppression of tinnitus was high in comparison to the degree of each volume load, that value was selected and adopted as a treatment schedule (RI effect for one time) of this patient.

Example

As illustrated in FIG. 11A, changes in the perceptual volume were predicted in a case where masker presentation and cessation were repeated at 10 second intervals. It was predicted that the tinnitus volume (TV) will decrease markedly the first time the masker sound is presented, and thereafter even if the volume of the masker sound is gradually lowered, TV will be controlled to a sufficiently low value, and therefore it was determined that this treatment program is sufficiently effective. Because the progress of TV can be simulated with respect to different treatment sounds and different volumes for individual patients, selection of the optimal treatment sound could be performed.

Example

As illustrated in FIG. 6, a program could be selected which delayed the tinnitus recovery process of tinnitus whose volume had been lowered once by RI or a long-time masker effect, by inhibiting perceptual drift by means of an efficient sound stimulus that caused a perception update in the subsequent recovery process.

With respect to patient A, it is derived from the RI effect curve of each sound source that, by RI, an effect of a tinnitus disappearance is obtained by presenting sound source S1 at a minimum of 50 dB for 10 seconds, and by a perception update induced by presenting sound source S2 (click sound) at 20 dB for 5 seconds, perceptual drift for recovery of tinnitus is inhibited and the tinnitus recovery time is delayed. By executing a program in which sound source S1 is presented at 50 dB for 10 seconds and thereafter sound source S2 is presented at 20 dB for 5 seconds, a state in which the tinnitus volume has been reduced can be maintained extremely efficiently from immediately after the treatment.

Example

[Creation of Treatment Sound Program Using TL Decrease Curve]

Example

As illustrated in FIG. 11B, it was inferred that, for 10 minutes, the TL decreases after sound source S2 is presented, and it was inferred that the TV is further effectively suppressed by lowering the volume of sound source S2 in accordance with the TL, and a program was executed.

This will be described using a specific example. Let us assume there is a patient for which: (1) characteristics of tinnitus are a pitch match of 6000 Hz and a volume of 70 dB; and (2) hearing ability falls abruptly in both ears across the upper range from 4000 Hz.

For this patient, based on the characteristics of the tinnitus, a program is determined that includes a treatment sound in which band noise or scale sounds of around 6000 Hz is adopted as the main body of the treatment sound and which is accompanied by noise or environmental sounds ranging from 4000 Hz to 8000 Hz based on the RI effect curve or the TL decrease curve obtained from the hearing impairment band, as well as temporal changes in the treatment sound. In tinnitus treatment device 10, selection of settings is made in accordance with the volume and volume balance and the like so that the treatment sound determined in this manner is reproduced.

Further, a technique that changes a treatment sound while being provided is as follows. With regard to the sound load determined before starting use of tinnitus treatment device 10, a change in the treatment sound, specifically, a change pertaining to selection of the two sounds, the balance of the volume, and adjustment of the overall volume is performed that reflects the subjective judgment of the patient after use is started, for example, the individual impression of the patient regarding the volume, pitch, or tone, respectively, of the treatment sound that is being output, a difference between the tinnitus suppression predicted by the program and the actual tinnitus suppression, or an impression such as pleasantness or unpleasantness, or a like or a dislike. This change can be immediately executed by the patient themselves using operation unit 300 of tinnitus treatment device 10 as described in the aforementioned section "Operation".

In tinnitus treatment device 10 that receives an input relating to such a subjective judgment, for example, in a case where the tinnitus suppression effect matches expectations and is good or the relevant input indicates a positive judgment of the patient such as "pleasant" or "like", output of the relevant treatment sound is continued. In a case where the tinnitus suppression effect is poor or the relevant input indicates a negative judgment of the patient such as "unpleasant" or "dislike", sound adjuster 240 uses the next best selection on the program, or makes a change to the settings for reproduction of the treatment sound such as lowering the volume, changing the pitch, or replacing one of the sounds that is being output in parallel with a different sound.

Further, information relating to the subjective judgment may be stored, for example, as one port of the treatment history data in storage 100. In addition, for example, in a case where there was an input indicating a negative judgment of the patient, the treatment sound may be changed to a treatment sound for which the patient indicated a positive judgment in the past.

Figure 19A:
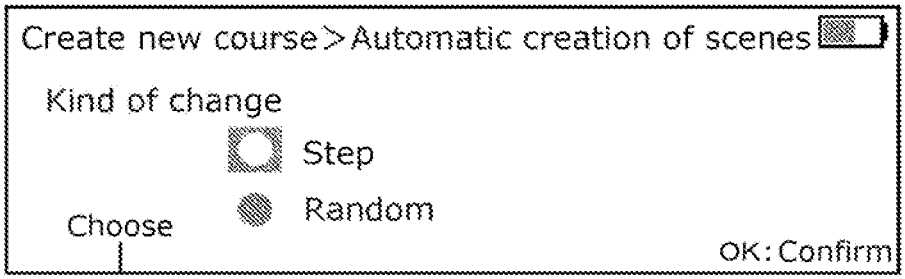
FIG. 19A is a diagram illustrating an example of a screen displayed on the tinnitus treatment device according to the embodiment.
Figure 19B:
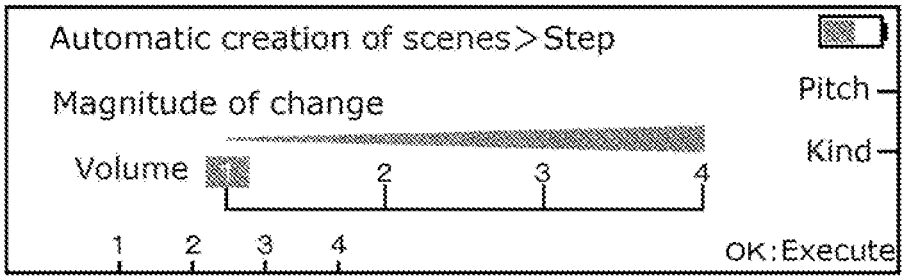
FIG. 19B is a diagram illustrating an example of a screen displayed on the tinnitus treatment device according to the embodiment.

Even then, it is not always the case that a treatment sound that is created and output by the above method is comfortable for the patient. For example, in a case where monotony feels uncomfortable to the patient, in some cases the treatment sound will feel comfortable by adding subtle changes over time thereto. However, in some cases there may be a limit to the addition of such changes to the treatment sound when the changes are only those which are made by a setting selected by the users including a patient, or the burden placed on the user by the operation required to make such a setting may be excessive. Such a problem can be resolved by, for example, in controller 200, every time that timer 210 measures a certain time period, sound adjuster 240 adds a random change such as a change in pitch, volume, or volume balance to the sound that is selected for the current scene. The presence or absence of such a random change is set, for example, on the screens illustrated in FIG. 19A and FIG. 19B, and the extent of the change is also adjusted.

Alternatively, another option is executed based on the RI effect curve and the TL decrease curve on the program.

Alternatively, sounds in which the volume, tone, or pitch change in a short time period, such as the high-pitched chirping of insects or the flow of a river may make tinnitus inaudible even at a low volume. Further, it is known empirically that such sounds have an effect of providing comfort to the listener. With tinnitus treatment device 10 that is capable of allowing a patient to listen to such an environmental sound alone or simultaneously with noise or a scale sound, comfort during use can be maintained while reducing the overall volume.

Thus, deciding the treatment sound in consideration of factors such as comfort and temporal changes is important for continuing treatment.

Further, it is considered that if data pertaining to examination results of the patient before providing a sound load, treatment sounds that were decided based on the examination results, and the effect of providing a sound load using tinnitus treatment device 10 is accumulated, a combination of treatment sounds or a standard example of temporal transition with which an effect is efficiently obtained can be derived based on the results of [a tinnitus] *an audibility* examination or a tinnitus examination or the results of both thereof.

[Setting of Sound Load Based on Determined Treatment Sound]

A single scene is determined by deciding a treatment sound including one or more sounds by the aforementioned technique, and deciding the settings for the reproduction level and the time length for reproducing the treatment sound. A course in which a plurality of such scenes are arranged in time series is, fundamentally, created by an efficient program by means of the RI effect curve and the TL decrease curve. In addition, it is possible to set a course by operations performed by a user as illustrated by an example in the aforementioned section "Operation". However, it is also considered that, in practice, there may also be cases where the operations and time required to determine the necessary number of treatment sounds for setting scenes that are different from each other will impose a heavy burden on the user.

A configuration may be adopted so that, based on settings included in such one scene or small number of scenes, the settings of another scene or even of a course including a plurality of scenes are automatically determined. More specifically, an appropriate scene group is automatically created by utilizing the RI effect curve or TL decrease curve which are mentioned above. By this means, setting of a course for providing an appropriate sound load to a user is efficiently determined with a small burden on the user, and use of tinnitus treatment device 10 is encouraged. A technique for setting such a plurality of scenes and a course will be described below using a specific example.

[Management of Volume Fluctuation in Frequency Band of Treatment Sound]

RI may occur when a sound in a frequency band that masks tinnitus is presented as a sound load for a predetermined length of time (several seconds) or longer and presentation of the sound load is then stopped.

Further, an effect that masks tinnitus is achieved even with a sound in which there are increases and decreases in volume at short intervals, such as environmental sounds like the chirping of crickets and the sound of water flowing. Because such a sound has a sufficient masking effect even at a volume that is smaller overall than noise in which there no changes or there are very small changes in volume, this effect can be quantified as a sound change stimulus.

In verification carried out by the inventor, it was confirmed that, with respect to a tinnitus masking effect that is obtained by presenting a sound load, the effect differs depending on the state of increase or decrease in the volume of the sound in a frequency band that at least partially overlaps with the frequency of the tinnitus that the patient perceives or the frequency at which the impairment in hearing ability exists, and quantification as a sound change stimulus was effective.

Further, by managing increases and decreases in volume at a specific frequency band, the volume increases and decreases can be utilized for the purpose of masking. In addition, not only natural sounds, but also sounds obtained by actively processing such natural sounds, and sounds that were synthesized from the start as artificial sounds can be utilized as treatment sounds in tinnitus treatment device 10 according to the present invention.

For example, data of the sound material of a sound of a certain insect is analyzed, and is recorded as data in which there are increases and decreases of 30 dB at intervals of 0.5 seconds in a band from 2000 Hz to 6000 Hz. In addition, similar elements are recorded with respect to data of large number of other sound materials. Furthermore, such sound material data may be processed according to the purpose. For example, a frequency band that fluctuates may be changed, or a degree of strength or weakness, or a time interval between fluctuations may be changed and utilized. These are stored as data as sound change stimuli, and are utilized in the next program.

Alternatively, without utilizing natural sounds, sounds may be created as purely artificial sounds that take into consideration these sound change stimuli, and utilized as sound material.

When utilizing the data of these sound materials, for example, the data is stored as sound material data in storage 100 and also registered in the sound material list. These pieces of data are then obtained by referring to the sound material list.

By analyzing and managing the data quantified as sound change stimuli in this way, scenes that achieve a masking effect for tinnitus with a lower volume can be created.

[Utilization of [tinnitus] *audibility* examination results]

As mentioned in the foregoing section "Setting of Sound Load", the result of [a tinnitus] *an audibility* examination of the patient is used to determine the treatment sound. Furthermore, nowadays, in [a tinnitus] *an audibility* examination that uses an instrument, the result is recorded as digital data, and with some limited instruments it is also possible to output such data to outside of the instrument. However, there are still many examination instruments or external devices or systems that do not support such data utilization, and there is also no common data specification (format) for which compatibility has been taken into consideration.

As a specific example, the result of the pure-tone audiometry examination which is considered a basic and important examination among auditory examinations is a result that indicates, for each frequency, the presence or absence of impairment and also the degree of impairment of the patient, and this result is useful for determining a treatment sound to be output from tinnitus treatment device 10. Although there are many items in the data for the result of a pure-tone audiometry examination, as mentioned above, because no standard specifications exist with regard to the data, utilizing the data outside of the examination instrument involves inconvenience.

The inventor of the present application proposes, as described hereunder, a method for reading in the result of [a tinnitus] *an audibility* examination of a patient as numerical value data, and utilizing the numerical value data to identify a hearing impairment band associated with tinnitus.

For example, it is possible to utilize a screen image displayed on a monitor or an image printed on paper as a result of [a tinnitus] *an audibility* examination.

Figure 20A:
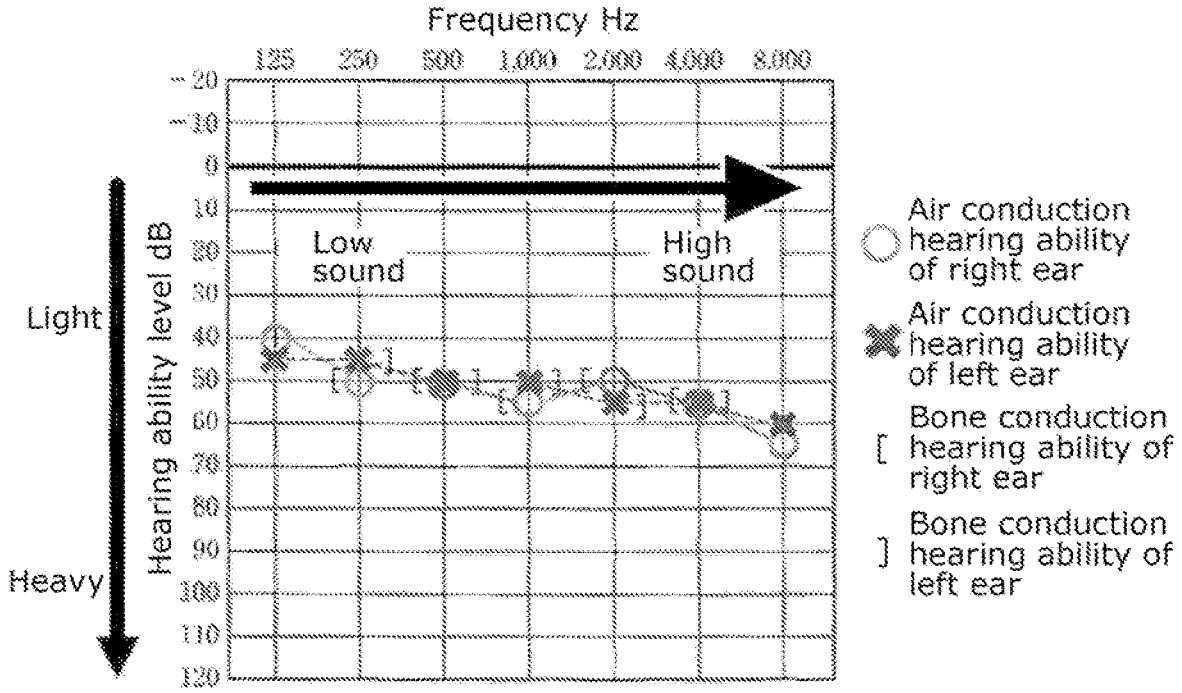
FIG. 20A is an image obtained by capturing a screen image of an examination result displayed on a monitor from one pure-tone audiometer.
Figure 20B:
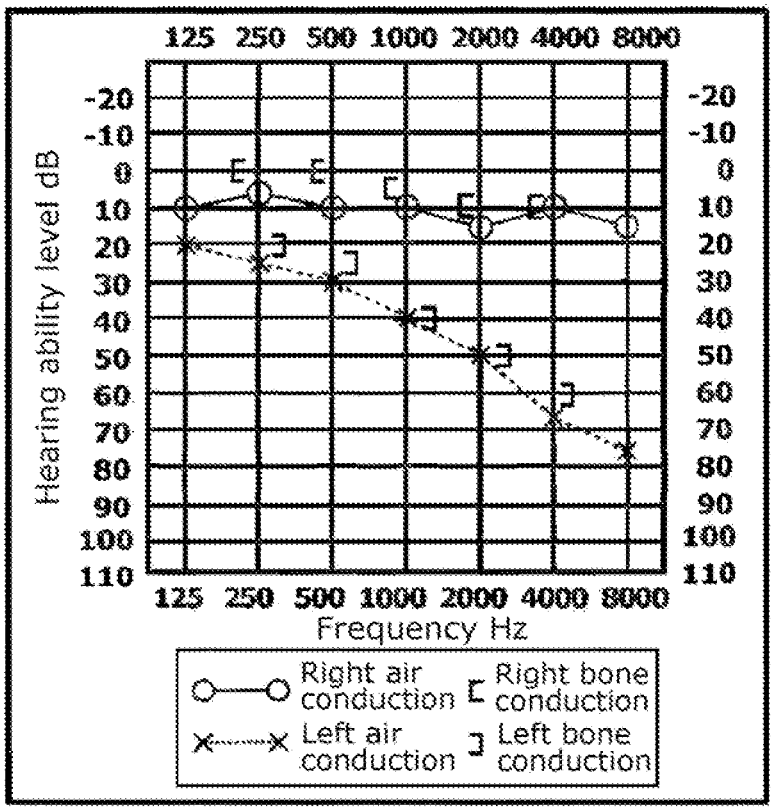
FIG. 20B is an image obtained by capturing a screen image of an examination result displayed on a monitor from another pure-tone audiometer.

As an example, a result of a pure-tone audiometry examination is illustrated in FIG. 20A and FIG. 20B. FIG. 20A and FIG. 20B illustrate images obtained by capturing a screen image of examination results displayed on a monitor from respectively different pure-tone audiometers. Note that, the patients that were the subjects of the examinations were different. Both screen images include symbols indicating numerical values of the examination result that are plotted within a graph region.

The result of a normal pure-tone audiometry examination is represented by numerical values for around 25 levels at intervals of 5 dB from −10 dB to 110 dB for each of the left and right ears that are tested at each of a total of 24 points which are made up of 7 points for testing air conduction hearing ability at frequencies from 125 Hz to 8000 Hz, and 5 points for testing bone conduction hearing ability at frequencies from 250 Hz to 4000 Hz. The examination results included in these image examples are also like this, and the amount of information is common.

In these images, in comparison to a technique for graphic recognition or character recognition in an image that is generally performed using image recognition software with an information processing apparatus (not illustrated) such as a computer, there are fewer symbols that are objects for recognition which indicate points, and there are also fewer levels of the numerical values which each symbol can indicate. Therefore, the numerical values of the examination result can be obtained relatively accurately by reading the image showing the examination result into an information processing apparatus capable of executing image recognition, and executing the image recognition.

Figures 21A, 21B:
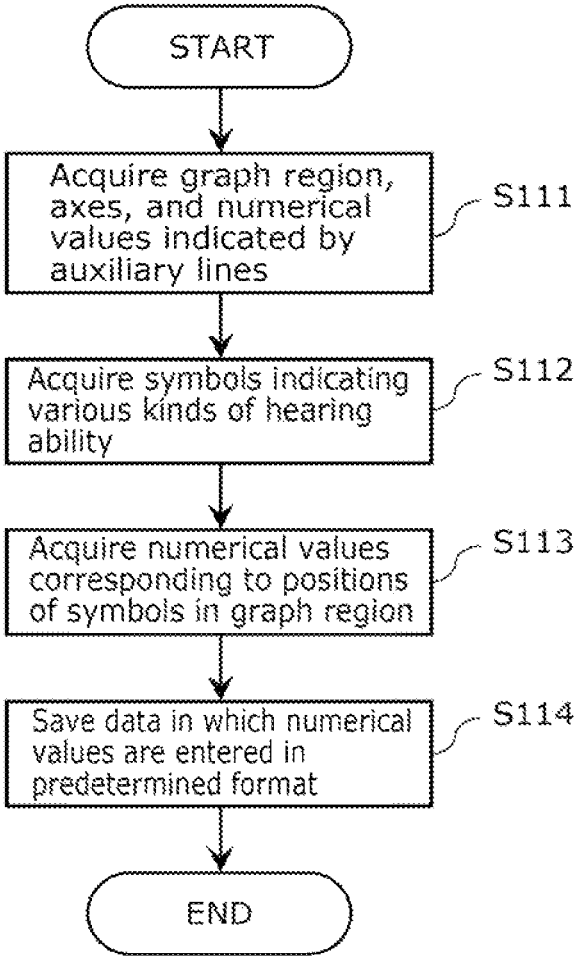
FIG. 21A is a flowchart of an example of procedures for acquiring numerical values of an examination result from an image of an examination result that was read in by an information processing apparatus.
FIG. 21B is a diagram illustrating an example of a predetermined format for storing numerical values of an examination result acquired from an image.

An example of procedures executed by such an information processing apparatus to acquire the numerical values of an examination result from an image that was read in is illustrated in the flowchart shown in FIG. 21A.

First, the axes of the graph region, auxiliary lines, and characters of the labels of the axes in the image that was read in are recognized, and the position, size and respective axes of the graph region as well as the numerical values which the auxiliary lines indicate are acquired (step S111).

Next, the legend portion within the image is identified, and the symbols indicating air conduction hearing ability and the symbols indicating bone conduction hearing ability for the left and right ears, respectively, are acquired (step S112).

Next, symbols indicating air conduction hearing ability and symbols indicating bone conduction hearing ability that are inside the graph region are found, and the numerical value corresponding to the position of each symbol is acquired based on the positional relation between each symbol and each auxiliary line (step S113).

Next, the numerical values acquired for the respective symbols entered at a position corresponding to the kind and position of the respective symbols in a predetermined format and saved (step S114). FIG. 21B is a diagram illustrating an example of the predetermined format. In this example, a table including respective fields for entering numerical values indicating air conduction hearing ability and numerical values indicating bone conduction hearing ability for the left and right ears, respectively, which were measured by a pure-tone audiometry examination is used as the predetermined format. In the example illustrated in FIG. 21B, numerical values acquired from the image shown in FIG. 20B are stored in the table.

Note that, the process for inputting the examination results into an information processing apparatus that executes image recognition and the type of data are not limited to the example described above. For example, it is possible to input the examination results by reading in a print-out using a scanner, transferring an image captured using a digital camera or a file in a format that can be an object of image recognition such as a PDF file, or storing the image or the file in a predetermined location.

Once the result of an examination have been converted into data of a predetermined format in this manner, it is easy to utilize the data interchangeably between devices. Because it is easy to utilize the result of an examination as numerical value data in an information processing apparatus, as well as of course being able to manage the data in a medical management system including electronic medical records, a large amount of data can be accumulated and can be an object of statistics and analysis.

The results of such analysis can be utilized in the development of a program into which data of the examination results of respective patients is input and which estimates impairment bands and severity, and infers the characteristics of tinnitus which is liable to occur in the respective patients. Recommended sound load settings that are based on the inferred tinnitus characteristics may also be output from such a program. Further, data of the examination result of a patient and data of the usage history of tinnitus treatment device 10 and the effect felt by the patient can be analyzed together, and can be utilized in the development of a program that accurately determines the settings of a sound load with which an effect is more easily obtained, based on the analysis result.

Such a method that extracts specific information that is the results of specific kinds of examinations from images of various formats that include the information in question and outputs the extracted information as data in a predetermined format may be realized by software that is executed by a processor on an information processing apparatus.

For example, the information processing apparatus may be a portable information terminal such as a smartphone, and the software may be provided, for example, as one part of software (a so-called "app") that causes the portable information terminal to function as tinnitus treatment device 10, and acquisition of image data can be performed by communication with an external device or the like, or may be performed using a camera that the portable information terminal is equipped with.

Further, the information processing apparatus may be a personal computer that can be separated from tinnitus treatment device 10, and in this case the use of data that is output from the software is not limited to use for selection of a treatment sound in tinnitus treatment device 10, and the data may be incorporated into an electronic medical record as described above or may be accumulated as material for research.

[Effectiveness of Present Invention]

Here, the usefulness of the present invention is verified while introducing treatment cases in which the inventor actually performed treatment of tinnitus patients using the present invention.

The intent here is not to discuss the appropriateness of the aforementioned hypothetical theory advanced by the inventor, but rather to support the technical significance and usefulness of the present invention with the effectiveness of the present invention for performing treatment based on this theory. Further, it is not intended to limit the features of the tinnitus treatment device and the like of the present invention by the following description.

[Overview]

By using tinnitus treatment device 10, the effect of a long-time masker which is also seen as the effect of the aforementioned masker therapy is obtained. The term "long-time masker" refers to an effect such that, when treatment is performed in which a patient is caused to listen to a treatment sound that masks tinnitus for a certain period of time, suppression of tinnitus is continuously recognized even after the treatment. Such an effect is seen in 60 to 70% of all patients.

Although in the conventional masker therapy, a masker produced with a single band noise that is fixed is assumed, in the case of the present device the treatment is reconfigured from the viewpoint of a TL decrease induced by presentation of a treatment sound for a long time period. It is assumed that changes to the frequency distribution or volume of the band noise can be flexibly performed, and that TL is decreased by the changed sound also.

In the case of the present device, the treatment is reconfigured also from the viewpoint of an RI effect induced by presenting the treatment sound for a shorter time period, and it is assumed that a perceptual drift and a perception update are utilized to control the tinnitus volume.

In the case of the present device, it is assumed that more effective tinnitus volume control is achieved by analyzing two elements in the treatment sound, namely, a sound pressure stimulus caused by a fixed sound and a sound change stimulus caused by a changed sound, and applying the two elements to both of the aforementioned TL decrease and RI effect to thereby analogize the effect of the treatment sound.

First, a treatment case in which treatment was performed using a tinnitus treatment device will be introduced. The tinnitus treatment device provides a sound stimulus for tinnitus treatment to a user who is a tinnitus patient on a unit time basis, and includes: a controller; and a recording medium in which a treatment program is stored. The treatment program is executed by the controller to perform: analogizing one or both of a residual inhibition (RI) effect curve and a TL decrease curve for tinnitus treatment sound provided to the user; generating the tinnitus treatment sound based on the one or both of the RI effect curve and the TL decrease curve which is analogized; and presenting the tinnitus treatment sound generated to the user via a sound presentation unit on the unit time basis to provide the sound stimulus to the user.

Twenty-three patients (13 males and 10 females) aged from 50 to 91 years old who had been affected by tinnitus for 1 year or more as subjects were subjected to a pure-tone audiometry examination, a pitch match test, a volume test, a masking test, a depression test, and a tinnitus handicap inventory (THI) test in advance.

Thereafter, treatment for a short time period (30 minutes) was administered by presentation of a treatment sound that was programmed by analogizing based on the RI effect curve. The presented sound was prepared so that frequency distributions of the band noises would match in opposite directions with respect to the frequency distribution curve of the hearing impairment region of each patient (for example, for hearing ability having a minimum peak of 30 dB at 2000 Hz, sound with a band of noise having a maximum peak at 2000 Hz). A volume of the presented sound at which tinnitus was completely masked was determined in the masking test, and band noise with a volume that was 10 dB higher than the thus-determined volume was adopted as the initial treatment sound.

Presentation of the presented sound conformed to the method illustrated in FIG. 11A in which presentation and silence were repeated at 10-second intervals. From the previous data, the relationship between a decrease in the volume of the presented sound and the TV could be analogized from the RI effect curve for patients with the same level of hearing impairment, pitch match, and volume. Since it could also be analogized that it is possible to maintain the TV at a low value even when the volume of the presented sound is gradually decreased, transitions in the volume of the presented sound that were expected to be optimal were programmed and executed.

Although at the current stage the number of patients as a statistical sample is small, it has been possible to execute extremely varied examinations using the present device and therefore a lot of information was obtained from each patient, and the grounds for inferring this kind of certain tendency were obtained.

Of the 23 patients, a group of 18 patients excluding three elderly patients aged 80 years or older and two patients with a strong hearing loss around the tinnitus who could hardly hear band noise was taken as "group A", and the RI effect was recognized in 16 (88.8%) of the group A patients.

The two patients in group A in which the RI effect was not seen had neurological symptoms, and it was difficult to test the pitch match and volume. Therefore, exclusion of patients with neurological symptoms would be expected to result in even better performance results overall.

A disappearance of tinnitus was recognized in 10 patients (55%) among the 18 patients of group A, with the tinnitus disappearance being progressively more noticeable as the age and degree of hearing loss of the patient decreased. For example, for patients aged 65 or under, a tinnitus disappearance was recognized in 6 out of 8 patients (75%).

Further, the lighter that hearing loss was in younger patients, the more dramatic the improvement effect that was recognized with a single band of noise. On the other hand, the stronger that hearing loss was in older patients, the greater the RI effect that was recognized by using a combination of a plurality of bands noises and tones.

The RI effect mentioned above was achieved within the first minute in all cases. The RI effect was maintained for 30 minutes thereafter in all 16 patients in which the effect was recognized.

According to the RI reports presented so far, it is reported that, for a single masker presentation, continuation of the RI effect lasts for a period from several seconds to several minutes. With respect to the current method, it is suggested that it is possible to maintain the RI effect for a long time.

In continuation from the aforementioned treatment for a short time period, a treatment sound was presented for five hours to the 18 patients of group A, and the long-term tinnitus suppression effect was examined from the viewpoint of a TL decrease.

The characteristics of TL, TV, and tinnitus (frequency distribution of tinnitus) after the end of the aforementioned short-time treatment (after 30 minutes after the start of the treatment) were calculated in advance using the RI effect curve, and at that time point (30 minutes after the start of the treatment), band noise which was approximately 10 dB higher than the respective frequencies of the tinnitus was presented to the respective patients for 10 minutes.

At that time point (40 minutes after the start of the treatment), with respect to TL that was calculated in advance using the TL decrease curve, band noise which was similarly approximately 10 dB higher than the respective frequencies was presented for the next 10 minutes.

At that time point (50 minutes after the start of the treatment), with respect to TL that was similarly inferred from the TL decrease curve, from the viewpoint of a sound change stimulus and a sound pressure stimulus, a sound source with a high sound change stimulus effect was selected and presented.

Note that, with respect to cases for which it was inferred that the TL was sufficiently small at that time point, the volume was set so as to be the minimum volume in a range in which the TL could be maintained. (That is, a sound source with a strong sound change stimulus and a weak sound pressure stimulus was used.)

Thereafter, the same sound source was presented at the same volume until 5 hours passed after the start of treatment.

With respect to the treatment for 5 hours, an effect (tinnitus attenuation, tinnitus disappearance) was recognized in 16 patients (88.8%), and with respect to all the patients for which an effect was recognized in the short-time treatment, effectiveness was also recognized in the subsequent treatment for 5 hours.

This exceeds the 60% to 70% in the reports relating to the effect of a long-time masker obtained by the conventional treatment.

In addition, since a method which lowers the tinnitus volume from an early stage by using the RI effect in the initial stages, and maintains a low tinnitus volume by using the effect of a TL decrease in the long term was used, rapid and continuous tinnitus volume control was enabled, and the volume of the sound stimulus during that time was minimal and it was possible to provide many patients with a high level of satisfaction.

It was found that the elderly people and the people with severe hearing loss were a major factor in lowering the performance results with respect to measurement of the effects of treatment with the present device. In other words, it is considered that the fact that the elderly people tended to have depression, a low level of comprehension and severe hearing loss, and also that masking cannot be sufficiently performed for people with severe hearing loss were the reasons for these low performance results.

It is highly significant that a therapeutic effect was achieved at a probability of around 90% in a large portion of the patients that were the subjects of the tinnitus treatment who were referred to as "group A" (under 80 years old, with normal age-related hearing loss). The inventor considers that the present invention will have an important influence on future tinnitus treatment.

Further, although in the conventional TRT it often takes half a year or more to improve on the results of the THI test, among patients who used the present device for three months or more, there were cases where the results of the THI test were already improving.

Among 14 patients, only one patient has stopped using the present device during the course of treatment, and the remaining 13 patients wish to continue using the present device.

Currently, according to the widely accepted theory described NPL 1, it is considered important to be incognizant of tinnitus, and indeed consciously manipulating the treatment sound has not been recommended until now.

However, the fact that THI is improved by the technique of the present device that actively manipulates and changes the treatment sound is a result that runs counter to the theory of NPL 1, and suggests the possibility of a novel tinnitus treatment.

Other Embodiments

Whilst the tinnitus treatment device according to one or more aspects has been described above based on an embodiment, the present invention is not limited to this embodiment. Other embodiments realized by application of various modifications conceivable by those skilled in the art to the present embodiment, and embodiments configured by combining constituent elements of different embodiments may also be included within the scope of the one or more aspects without departing from the gist of the present invention.

For example, the number of sounds that are output in parallel as a treatment sound is not limited to two. Two sounds is merely an example, and three or more sounds may be output in parallel.

Further, although in the embodiment described above a plurality of pieces of sound material data that indicate sounds of band noise that are different to each other and two or more sounds that are not band noise, respectively, are stored in storage 100, these sounds do not necessarily have to be stored as individual pieces of data in storage 100. For example, by storing sound material data of noise serving as a base, such as white noise, in advance in storage 100, and applying filters in a multiple manner (for example, performing an operation in which a plurality of kinds of band-pass filters are applied in parallel) to the sound material data of the noise serving as a base that is read out from storage 100, the sounds of noise of a plurality of bands may be dynamically generated and output in parallel.

Furthermore, a sound indicated by sound material data stored in storage 100 may not be included in the treatment sound, and only a sound indicated by sound material data that is generated by such filtering and acquired by controller 200, or sound material data generated and acquired using a Fourier coefficient or a parameter of an FM sound source may be output as treatment sound.

Furthermore, the kinds of sound settings performed using operation unit 300 are not limited to the sound settings described above. For example, it may be possible to select various kinds of acoustic processing to be applied to a sound indicated by the sound material data. Examples of various kinds of acoustic processing that may be mentioned include processing that imparts effects referred to as a filter (a band-pass filter, a band-stop filter, a low-cut filter, or a high-cut filter or the like, or a combination of these filters), an equalizer, an echo, a reverb, a delay, a chorus, a phaser, a flanger, a compressor, and a limiter. A plurality of these acoustic processes may be applied in combination.

Further, it is not the case that all of the kinds of sound settings mentioned above are essential in tinnitus treatment device 10. For example, selection of a plurality of sounds and setting of the volume of each sound through operation unit 300 may be performed by combining the selection of each of the plurality of sounds and the setting of the absolute volume of each sound that is selected. Alternatively, the selection of a plurality of sounds and setting of the volume of each sound may be realized by combining the selection of each of the plurality of sounds, and selection of the respective settings for a ratio between the plurality of volumes, and the volume of the overall treatment sound.

Further, data that is used for selection of a treatment sound in controller 200 is not limited to the data mentioned thus far. In addition to the data mentioned above, for example, data indicating any one or more items among a patient's age, gender, psychological test result, case history, and sleep circumstances such as insomnia may also be used. It is known that there is some degree of correlation between these attributes or circumstances of a patient and symptoms of hearing ability abnormality or tinnitus. This suggests that a correlation exists between such information and the improvement of tinnitus caused by the treatment sound or the sound load. Therefore, controller 200 can receive data showing information relating to these attributes or circumstances of the patient as an input, and can further use data indicating a correlation between this information and the effect of the treatment sound or the sound load to accurately select a sound load that has a greater effect.

Further, although it is described above that charging to a chargeable battery is possible in a case where tinnitus treatment device 10 is realized as a portable device, it need not be possible to perform charging. Tinnitus treatment device 10 that is realized as a portable device may include a power source that acquires electric power from only a disposable battery, and supplies the electric power to each constituent element.

Furthermore, instead of, or in addition to, pitch or volume, the results of the tinnitus examination used to determine a treatment sound may include linguistic expressions such as onomatopoeic words or metaphors used by the patient to express the tinnitus. For example, linguistic expressions with a certain degree of variation and various treatment sounds may be associated statistically or acoustically in advance, and the treatment sounds may be selected according to this association. Further, the selected sound may be further subjected to adjustment according to an expression that modifies (for example, higher, lower, nearer to something, or a combination of two) the aforementioned linguistic expression. Even in such a case, selection of a treatment sound which approximates the tinnitus in terms of tone in addition to magnitude and pitch, or which is suitable for masking the tinnitus is accurately performed more easily.

Further, the present invention may be realized not only as a tinnitus treatment device, but may also be realized as a program for causing a portable information terminal as illustrated in FIG. 17A to function as a tinnitus treatment device. That is, the present invention may be realized as a program that controls a tinnitus treatment device, the tinnitus treatment device including a controller and being a device that provides a sound stimulus for tinnitus treatment to a user who is a tinnitus patient on a unit time basis, the treatment program being executed by the controller to: analogize one or both of an RI effect curve and a TL decrease curve for each tinnitus treatment sound provided to the user; generate the tinnitus treatment sound based on one or both of the RI effect curve and the TL decrease curve which is analogized; and present the generated tinnitus treatment sound to the user on a unit time basis via a sound presentation unit for presenting a tinnitus treatment sound that provides a sound stimulus to the user, to thereby provide the sound stimulus to the user.

INDUSTRIAL APPLICABILITY

The tinnitus treatment device or the like according to the present invention is applicable as a device or the like that outputs a treatment sound to be used for suppressing or alleviating the tinnitus of a tinnitus patient.

REFERENCE SIGNS LIST

10 tinnitus treatment device
20 loudspeaker (sound presentation unit)
100 storage
110 sound material data
120 sound material list
130 course data
140 treatment plan data
150 treatment history data
200 controller
210 timer
220 synthetic sound generator
230 sound material data obtainer
240 sound adjuster
250 sound output unit
260 sound load statistical unit
300 operation unit
310 volume operation unit
320 tone operation unit
330 pitch operation unit
400 display unit

The invention claimed is:

1. A tinnitus treatment device that provides a sound stimulus for tinnitus treatment to a user who is a tinnitus patient on a unit time basis, the tinnitus treatment device comprising:

a controller; and a recording medium in which a treatment program is stored, wherein the treatment program is executed by the controller to perform:

analogizing one or both of a residual inhibition (RI) effect curve and a TL decrease curve for tinnitus treatment sound provided to the user;

generating the tinnitus treatment sound based on the one or both of the RI effect curve and the TL decrease curve which is analogized; and presenting the tinnitus treatment sound generated to the user via a sound presentation unit on the unit time basis to provide the sound stimulus to the user.

2. The tinnitus treatment device according to claim 1, wherein the RI effect curve indicates, as progress of a tinnitus volume, RI effects before and after provision of [the] *a specific* sound stimulus *to a specific user*, the RI effect curve indicates the progress during a period in which the presenting of the tinnitus treatment sound begins, ends, and the tinnitus volume at the end of the presenting returns to the tinnitus volume before the presenting, *and* in the analogizing of the RI effect curve, RI effect curves of specific tinnitus treatment sound provided to a specific group of tinnitus patients each being the user are analogized based on one or more typical RI effect curves.

3. The tinnitus treatment device according to claim 1, wherein for each of users each being the user, the analogizing of the RI effect curve includes scaling the one or more typical RI effect curves linearly or nonlinearly along one or both of a time axis and a volume axis, under assumption that a time change of a tinnitus volume approaches a specific value while the sound stimulus is constant.

4. The tinnitus treatment device according to claim 1, wherein the TL decrease curve indicates a time change of a tinnitus volume during a period in which [the] *a specific* sound stimulus is provided *to a specific user*, *and* in the analogizing of the TL decrease curve, TL decrease curves of specific tinnitus treatment sound provided to a specific group of tinnitus patients each being the user are analogized based on one or more typical TL decrease curves.

5. The tinnitus treatment device according to claim 1, wherein for each of users each being the user, the analogizing of the TL decrease curve includes scaling the one or more typical TL decrease curves linearly or nonlinearly along one or both of a time axis and a volume axis.

6. The tinnitus treatment device according to claim 1, wherein in the presenting performed in the treatment program, the tinnitus treatment sound generated is presented to the user during a period in which a tinnitus volume of the user that is decreased from an initial tinnitus volume by RI effect or long-time masker effect returns to the initial tinnitus volume after being decreased, the tinnitus treatment sound providing a sound stimulus causing perception update.

7. The tinnitus treatment device according to claim 1, wherein the treatment program further performs:

subtracting, from (a1) an integrated amount of sound stimuli related to TL decrease, (b1) a sound pressure stimulus related to TL decrease to obtain (c1) a sound change stimulus related to TL decrease, (a1) the integrated amount indicating an amount of TL decrease of the user presented with the tinnitus treatment sound having a predetermined volume during a predetermined period, (b1) the sound pressure stimulus indicating an amount of TL decrease of the user presented, during the predetermined period, with sound having values fixed to an average value of volumes, an average value of pitches, and an average value of tones of the tinnitus treatment sound during the predetermined period, (c1) the sound change stimulus being regarding the tinnitus treatment sound; and analogizing, for a tinnitus treatment sound different from the tinnitus treatment sound or for a tinnitus patient different from the user, at least one of (a2) an integrated amount of sound stimuli related to TL decrease, (b2) a sound pressure stimulus related to TL decrease, and (c2) a sound change stimulus related to TL decrease, in accordance with (c1) the sound change stimulus obtained in the subtracting.

8. The tinnitus treatment device according to claim 1, wherein the treatment program further performs:

subtracting, from (a1) an integrated amount of sound stimuli related to RI effect, (b1) a sound pressure stimulus related to RI effect to obtain (c1) a sound change stimulus related to RI effect, (a1) the integrated amount indicating an amount of RI effect of the user presented with the tinnitus treatment sound having a predetermined volume during a predetermined period, (b1) the sound pressure stimulus indicating an amount of RI effect of the user presented, during the predetermined period, with sound having values fixed to an average value of volumes, an average value of pitches, and an average value of tones of the tinnitus treatment sound during the predetermined period, (c1) the sound change stimulus being regarding the tinnitus treatment sound; and analogizing, for a tinnitus treatment sound different from the tinnitus treatment sound or for a tinnitus patient different from the user, at least one of (a2) an integrated amount of sound stimuli related to RI effect, (b2) a sound pressure stimulus related to RI effect, and (c2) a sound change stimulus related to RI effect, in accordance with (c1) the sound change stimulus obtained in the subtracting.

9. The tinnitus treatment device according to claim 1, wherein the treatment program is executed by the controller to further perform:

obtaining a value indicating a result of at least one of [tinnitus] *audibility* examination and tinnitus examination of the user; and selecting a setting for reproducing the tinnitus treatment sound based on the value obtained.

10. The tinnitus treatment device according to claim 9, wherein the result of the tinnitus examination is at least one of:

a result including at least one of a pitch expressing tinnitus, a volume expressing the tinnitus, and a linguistic expression of a tone of tinnitus which is expressed by the user; and a result indicating mask sound shielding the tinnitus when the user listens to the mask sound.

11. The tinnitus treatment device according to claim 9, wherein the setting for reproducing the tinnitus treatment sound is performed based on data indicating a correlation related to tinnitus treatment effect between (i) tinnitus treatment sound producing tinnitus treatment effect when the user listens to the tinnitus treatment sound and (ii) the result of the at least one of the [tinnitus] *audibility* examination and the tinnitus examination.

12. The tinnitus treatment device according to claim 1, further comprising:

a power source that receives power from a battery, wherein the controller is driven with supply of the power received by the power source from the battery.

13. A *non-transitory computer-readable recording medium having recorded thereon a* tinnitus treatment program that controls a tinnitus treatment device, the tinnitus treatment device including a controller and being a device that provides a sound stimulus for tinnitus treatment to a user who is a tinnitus patient on a unit time basis, the *tinnitus* treatment program being executed by the controller to perform:

analogizing one or both of a residual inhibition (RI) effect curve and a TL decrease curve for tinnitus treatment sound provided to the user;

generating the tinnitus treatment sound based on the one or both of the RI effect curve and the TL decrease curve which is analogized; and presenting the tinnitus treatment sound generated to the user via a sound presentation unit on the unit time basis to provide the sound stimulus to the user.

* * * * *